US010457928B2

(12) United States Patent
Hellmuth et al.

(10) Patent No.: US 10,457,928 B2
(45) Date of Patent: Oct. 29, 2019

(54) PROTEASE VARIANTS HAVING AN IMPROVED WASHING PERFORMANCE

(71) Applicant: Henkel AG & Co. KGaA, Duesseldorf (DE)

(72) Inventors: Hendrik Hellmuth, Darmstadt (DE); Thomas Weber, Dormagen (DE); Timothy O'Connell, Landsberg am Lech (DE); Susanne Tondera, Duesseldorf (DE); Brian Laufs, Juechen (DE); Ayhan Aydemir, Duesseldorf (DE); Claudia Lindner, Solingen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/532,829

(22) PCT Filed: Dec. 1, 2015

(86) PCT No.: PCT/EP2015/078131
§ 371 (c)(1),
(2) Date: Jun. 2, 2017

(87) PCT Pub. No.: WO2016/087403
PCT Pub. Date: Jun. 9, 2016

(65) Prior Publication Data
US 2018/0023069 A1   Jan. 25, 2018

(30) Foreign Application Priority Data
Dec. 4, 2014   (DE) .......................... 10 2014 224 825

(51) Int. Cl.
*C12N 9/52* (2006.01)
*C12N 9/54* (2006.01)
*C11D 3/386* (2006.01)

(52) U.S. Cl.
CPC ............... *C12N 9/54* (2013.01); *C11D 3/386* (2013.01); *C12Y 304/21062* (2013.01)

(58) Field of Classification Search
None
See application file for complete search history.

(56) References Cited

U.S. PATENT DOCUMENTS

| 6,287,841 | B1 * | 9/2001 | Mulleners | ............... | C11D 3/386 |
| | | | | | 435/221 |
| 2004/0259222 | A1 | 12/2004 | Breves et al. | | |
| 2005/0043198 | A1 * | 2/2005 | Weber | ..................... | C11D 3/386 |
| | | | | | 510/320 |
| 2009/0275493 | A1 * | 11/2009 | Siegert | ..................... | A61K 8/66 |
| | | | | | 510/320 |
| 2012/0238005 | A1 * | 9/2012 | Wieland | ................. | C11D 3/361 |
| | | | | | 435/264 |
| 2013/0005637 | A1 * | 1/2013 | Siegert | ................... | C11D 3/386 |
| | | | | | 510/392 |
| 2013/0280794 | A1 | 10/2013 | Wieland et al. | | |

FOREIGN PATENT DOCUMENTS

| WO | 0060060 A2 | 10/2000 | |
| WO | 03054177 A2 | 7/2003 | |
| WO | 2007079938 A2 | 7/2007 | |
| WO | WO-2008086916 A1 * | 7/2008 | ............... A61K 8/66 |

OTHER PUBLICATIONS

Guo et al., Protein tolerance to random amino acid change, Proc. Natl. Acad. Sci. USA, 2004, 101, 9205-10.*
Jakob et al., Surface charge engineering of a Bacillus gibsonii subtilisin protease, Appl. Microbiol. Biotechnol., Nov. 2012, 97, 6793-6802.*
EPO, International Search Report and Written Opinion issued in International Application No. PCT/EP2015/078131, dated May 9, 2016.
Altschul et al.: "Basic Local Alignment Search Tool," Journal of Molecular Biology, 1990, pp. 403-410, vol. 215.
Altschul et al.: "Gapped BLAST and PSI-BLAST: a New Generation of Protein Database Search Programs", Nucleic Acids Research, 1997, pp. 3389-3402, vol. 25, No. 17.
Bender et al, "The Determination of the Concentration of Hydrolytic Enzyme Solutions: a-Chymotrypsin, Trypsin, Papain, Elastase, Subtilisin, and Acetylcholinesterase", Journal of the American Chemical Society, 1966, pp. 5890-5913, vol. 88, No. 24.
Bryan, P.N., "Protein engineering of subtilisin," Biochimica et Biophysica Acta, Dec. 29, 2000, pp. 203-222, vol. 1543, No. 2.
Chenna et al.: "Multiple Sequence Alignment with the Clustal Series of Programs", Nucleic Acids Research, 2003, pp. 3497-3500, vol. 31, No. 13.
Delmar, E.G., et al. "A Sensitive New Substrate for Chymotrypsin1," Analytical Biochemistry, Nov. 1979, pp. 316-320, vol. 99, No. 2.
Gornall et al., "Determination of Serum Proteins by Means of the Biuret Reaction", Journal of Biological Chemistry, Feb. 1949, pp. 751-766, vol. 177, No. 2.
Maurer, K-H, "Detergent Proteases," Current Opinion in Biotechnology, Aug. 2004, pp. 330-334, vol. 15, No. 4.
Notredame et al.: "T-Coffee: A Novel Method for Fast and Accurate Multiple Sequence Alignment", Journal of Molecular Biology, Sep. 8, 2000, pp. 205-217, vol. 302, No. 1.

(Continued)

*Primary Examiner* — Robert B Mondesi
*Assistant Examiner* — Todd M Epstein
(74) *Attorney, Agent, or Firm* — Lorenz & Kopf, LLP

(57) ABSTRACT

The disclosure relates to proteases, the amino acid sequence of which has been modified in particular with regard to the use thereof in detergents and cleaning agents, all sufficiently similar proteases having a corresponding modification and nucleic acids coding for them. The disclosure further relates to methods and uses of said proteases and to agents containing them, in particular detergents and cleaning agents.

4 Claims, No Drawings
Specification includes a Sequence Listing.

(56) References Cited

OTHER PUBLICATIONS

Sambrook, J., et al. "Molecular Cloning: A Laboratory Manual," Second Edition, 1989, Cold Spring Harbor Laboratory Press, Cold Spring Harbor, NY, vol. 1-3.
Sambrook, J., et al. "Molecular Cloning: A Laboratory Manual," Third Edition, Jan. 15, 2001, Cold Spring Harbor Laboratory Press, Cold Spring Harbor, NY, vol. 1-3.
Siezen, R.J. "Subtilases: Subtilisin-like Serine Proteases," Subtilisin Enzymes: Practical Protein Engineering, 1996, pp. 75-93, Plenum Press, New York and London.
Van Raay et al, "The Determination of Proteolytic Activity in Enzyme Concentrates and Enzyme Containing Detergents", Tenside Detergents, May 1970, pp. 125-132, vol. 7, No. 3.

* cited by examiner

PROTEASE VARIANTS HAVING AN IMPROVED WASHING PERFORMANCE

CROSS-REFERENCE TO RELATED APPLICATION

This application is a U.S. National-Stage entry under 35 U.S.C. § 371 based on International Application No. PCT/EP2015/078131, filed Dec. 1, 2015, which was published under PCT Article 21(2) and which claims priority to German Application No. 10 2014 224 825.6, filed Dec. 4, 2014, which are all hereby incorporated in their entirety by reference.

TECHNICAL FIELD

The disclosure lies in the field of enzyme technology. The disclosure relates to proteases of which the amino acid sequence has been modified in particular in regard to the use thereof in detergents and cleaning agents, all sufficiently similar proteases having a corresponding modification and nucleic acids coding for them. The disclosure further relates to methods and uses of said proteases and to agents containing them, in particular, detergents and cleaning agents.

BACKGROUND

Proteases belong to the industrially most important enzymes. For detergents and cleaning agents, they are the longest established enzymes and are contained in virtually all modern, powerful detergents and cleaning agents. They cause the breakdown of protein-containing stains from the item to be cleaned. Among them, proteases of the subtilisin type (subtilases, subtilopeptidases, EC 3.4.21.62) are particularly important, which are serine proteases due to the catalytically active amino acids. They act as unspecific endopeptidases and hydrolyze any acid amide bonds located inside peptides or proteins. Their pH optimum is usually within the distinctly alkaline range. An overview of this family is provided, for example, by the article "Subtilases: Subtilisin-like Proteases" by R. Siezen, pages 75-95 in "Subtilisin enzymes," edited by R. Bott and C. Betzel, New York, 1996. Subtilases are naturally formed by microorganisms. Special mention should be made of the subtilisins formed and secreted in particular by the *Bacillus* species as the most important group within the subtilases.

Examples of the proteases of the subtilisin type preferably used in detergents and the cleaning agents are subtilisins BPN' and Carlsberg, protease PB92, subtilisins 147 and 309, the protease from *Bacillus lentus*, in particular from *Bacillus lentus* DSM 5483, subtilisin DY and the subtilases, but no longer the enzymes thermitase, proteinase K and proteases TW3 and TW7 associated with the subtilisins in the narrower sense, and variants of said proteases that have a modified amino acid sequence compared to the starting protease. Proteases are deliberately or randomly modified by methods known from the prior art and are optimized for example for use in detergents and cleaning agents. These include point mutagenesis, deletion or insertion mutagenesis, or fusion with other proteins or protein parts. Correspondingly optimized variants are thus known for most proteases known from the prior art.

BRIEF SUMMARY

A protease is provided herein. The protease includes an amino acid sequence which is identical to the amino acid sequence specified in SEQ ID NO. 1 or SEQ ID NO. 2 over the total length thereof to an extent of at least 70%. The protease further includes the amino acid D at position 97 and/or the amino acid E at position 99 in the numbering according to SEQ ID NO. 1.

A method for producing a protease is also provided herein. The method includes the step of introducing an amino acid substitution N97D and/or R99E in the numbering according to SEQ ID NO. 1 into a starting protease identical to the amino acid sequence specified in SEQ ID NO. 1 over the total length thereof to an extent of at least 70%, or introducing an amino acid substitution S97D and/or S99E in the numbering according to SEQ ID NO. 1 into a starting protease identical to that specified in SEQ ID NO. 2 over the total length thereof to an extent of at least 70%.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly been found that specific variants of the alkaline protease from *Bacillus gibsonii* (DSM14391) [Seq. ID 1] and the protease from *Bacillus* sp. (DSM 14392) [Seq. ID 2] or sufficiently similar proteases (based on the sequence identity) are particularly suitable for use in washing or cleaning agents and are improved in terms of the washing performance.

The subject of the present disclosure is therefore a protease which comprises an amino acid sequence which is identical to the amino acid sequence specified in SEQ ID NO. 1 or SEQ ID NO. 2 over the total length thereof to an extent of at least 70% and increasingly preferably to an extent of at least 75%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 99%, and which comprises the amino acid D at position 97 and/or the amino acid E at position 99 in the numbering according to SEQ ID NO. 1.

Preferably, the protease as contemplated herein comprises one or more amino acid substitutions, which are selected from N97D, S97D, R99E and S99E, in the numbering according to SEQ ID NO. 1.

Particularly preferred proteases are those of which the amino acid sequences are identical to the amino acid sequences specified in Seq. ID 4 to 9.

Another subject as contemplated herein is a method for producing a protease comprising the step of introducing an amino acid substitution N97D, S97D, R99E, or S99E, in the numbering according to SEQ ID NO. 1, into a starting protease which is identical to the amino acid sequence specified in SEQ ID NO. 1 or SEQ ID NO. 2 over the total length thereof to an extent of at least 70% and increasingly preferably to an extent of at least 75%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 99%.

Amino acid positions that are specified within the scope of the present disclosure by the wording "numbering according to SEQ ID NO. 1," are understood as follows: The other amino acid positions are defined by an alignment of the amino acid sequence of a protease as contemplated herein having the amino acid sequence of the protease from *Bacil-*

*lus gibsonii* (DSM 14391), as specified in SEQ. ID NO. 1. Furthermore, the assignment of the positions is based on the ripe (mature) protein. This assignment is particularly applicable when the amino acid sequence of a protease as contemplated herein comprises a higher number of amino acid residues than the protease from *Bacillus gibsonii* according to SEQ ID NO. 1. Starting from the mentioned positions in the amino acid sequence of the protease from *Bacillus gibsonii*, the modified positions in a protease as contemplated herein are those which are associated with these same positions in an alignment. For example, the protease according to SEQ ID NO. 2 has 374 amino acids. In alignment with the protease according to SEQ ID NO.1, it therefore follows that the positions 97 and 99 according to the numbering of SEQ ID NO. 1 correspond to positions 202 and 204 in the actual amino acid sequence of SEQ ID NO. 2.

A protease according to the present patent application comprises both the protease as such and a protease produced by a method as contemplated herein. Therefore, all references to a protease refer to both the protease as a substance as well as to the corresponding method, in particular production method of the protease.

Other subjects of the present disclosure are nucleic acids coding for proteases as contemplated herein, non-human host cells containing proteases or nucleic acids as contemplated herein, and agents comprising proteases as contemplated herein, especially detergents and cleaning agents, washing and cleaning methods, and uses of the proteases as contemplated herein, in particular in detergents and cleaning agents.

An inventive N97D, S97D, R99E and/or S99E modification in a protease comprising an amino acid sequence identical to an extent of at least 70% to the amino acid sequence specified in SEQ ID NO. 1 preferably results in an improved cleaning performance of this modified protease in detergents and cleaning agents on at least one protease-sensitive stain. Consequently, proteases as contemplated herein allow improved removal of at least one, preferably of more protease-sensitive stains on fabrics and/or hard surfaces, for example tableware. Particularly advantageous cleaning performances are demonstrated by preferred embodiments of proteases as contemplated herein on blood-containing stains, for example, on the stains blood and milk/ink on cotton: product no. C-05 available from CFT (Center For Test Materials) B.V. Vlaardingen, Netherlands and whole egg/pigment on cotton: product no. 10N available from wfk—Cleaning Technology Institute e.V., Krefeld, Germany.

Preferred embodiments of the present disclosure provide dirt-specific proteases of which the cleaning performance is improved specifically in terms of a stain or a number of stains of similar type, especially in terms of stains containing blood and whole egg.

Preferred embodiments of inventive proteases achieve such advantageous cleaning performances even at low temperatures, in particular in the temperature ranges between 10° C. and 60° C., preferably between 15° C. and 50° C., and particularly preferably between 20° C. and 40° C. Other preferred embodiments of inventive proteases achieve such advantageous cleaning performances in a wide temperature range, for example between 15° C. and 90° C., preferably between 20° C. and 60° C.

The term "cleaning performance" within the scope as contemplated herein is understood to mean the brightening performance on one or more stains, and in particular on laundry or tableware. In the context as contemplated herein, both the detergent or cleaning agent which comprises the protease or the washing or cleaning liquor formed by this agent, as well as the protease itself has a corresponding cleaning performance. The cleaning performance of the enzyme thereby contributes to the cleaning performance of the agent or of the washing or cleaning liquor formed by the agent. The cleaning performance is preferably determined as indicated further below.

A protease as contemplated herein has a proteolytic activity, that is, it is capable of the hydrolysis of peptide bonds of a polypeptide or protein, in particular in a detergent or cleaning agent. A protease as contemplated herein is therefore an enzyme which catalyzes the hydrolysis of peptide bonds and thus is capable of cleaving peptides or proteins. Furthermore, a protease as contemplated herein is preferably a ripe (mature) protease, i.e. the catalytically active molecule without the signal(s) and/or propeptide(s). Unless otherwise indicated, the sequences indicated also relate in each case to mature enzymes.

The determination of the identity of nucleic acid or amino acid sequences is performed by a sequence comparison. This sequence comparison is based on the commonly used BLAST algorithm established in the prior art (for example, see Altschul, S. F., Gish, W., Miller, W., Myers, E. W. & Lipman, D. J. (1990) "Basic local alignment search tool." J. Mol. Biol. 215: 403-410, and Altschul, Stephen F., Thomas L. Madden, Alejandro A. Schaffer, Jinghui Zhang, Zhang Hheng, Webb Miller, and David J. Lipman (1997): "Gapped BLAST and PSI-BLAST: a new generation of protein database search programs," Nucleic Acids Res., 25, pages 3389-3402) and is achieved principally in that similar sequences of nucleotides or amino acids in the nucleic acid or amino acid sequences are assigned to each other. A tabular assignment of the positions in question is referred to as alignment. A further algorithm available in the prior art is the FASTA algorithm. Sequence comparisons (alignments), especially multiple sequence comparisons, are created with computer programs. For example, the Clustal series (see, for example, Chenna et al (2003): Multiple sequence alignment with the Clustal series of programs Nucleic Acid Research 31, 3497-3500.), T-coffee (see, for example, Notre Dame et al. (2000): T-Coffee: A novel method for multiple sequence alignments J. Mol. Biol. 302, 205-217) or programs based on these programs or algorithms are frequently used. In the present patent application, all sequence comparisons (alignments) with the computer program Vector NTI® Suite 10.3 (Invitrogen Corporation, 1600 Faraday Avenue, Carlsbad, Calif., USA) were created with the predefined standard parameters, of which the AlignX module for sequence comparisons is based on ClustalW.

Such a comparison also allows a statement with regard to the similarity between the sequences being compared. It is generally expressed in percent identity, i.e. the proportion of identical nucleotides or amino acid residues at the same positions or in positions corresponding to one another in an alignment. The broader concept of homology, in the case of amino acid sequences, also takes into consideration conserved amino acid substitutions i.e. amino acids with similar chemical activity, since these usually exert similar chemical activities within the protein. Therefore, the similarity between the sequences being compared can also be specified as percent homology or percent similarity. Identity and/or homology information can refer to whole polypeptides or genes or only to individual regions. Homologues or identical regions of different nucleic acid or amino acid sequences are therefore defined by similarities in the sequences. Such regions often have identical functions. They may be small and include only a few nucleotides or amino acids. Often, such small regions exert essential functions for the overall activity of the protein. It may therefore be useful to relate sequence matches only to individual, possibly small regions. Unless otherwise stated, however, identity or homology information in the present application refers to the overall length of the indicated nucleic acid or amino acid sequence.

The cleaning performance of a protease as contemplated herein preferably corresponds to at least that of a protease comprising an amino acid sequence corresponding to the amino acid sequence specified in SEQ ID NO. 1, and/or at least that of a protease comprising an amino acid sequence corresponding to the amino acid sequence specified in SEQ ID NO. 3, wherein the cleaning performance is determined in a washing system containing a detergent in a dose from 4.5 to 7.0 grams per liter of washing liquor and the protease, wherein the proteases to be compared are used in equal concentration (based on active protein) and the cleaning performance in respect of a blood stain or a whole egg stain on cotton, in particular in respect of the stain blood and milk/ink on cotton: product no. C-05 available from CFT (Center For Test Materials) B.V. Vlaardingen, Netherlands or whole egg/pigment on cotton: product no. 10N available from wfk—Cleaning Technology Institute e.V., Krefeld, Germany, is determined by measuring the whiteness of the washed textiles, the washing operation is performed for 70 minutes at a temperature of 40° C., and the water has a water hardness from 15.5 to 16.5° (German hardness). The concentration of the protease in the detergent intended for this washing system is from 0.001 to 0.1 wt. %, preferably from 0.01 to 0.06 wt. %, in relation to active protein.

A preferred liquid detergent for such a washing system is composed as follows (all amounts in weight percent): 0.3-0.5% xanthan, 0.2-0.4% anti-foaming agent, 6-7% glycerol, 0.3-0.5% ethanol, 4-7% FAEOS (fatty alcohol ether sulfate), 24-28% non-ionic surfactants, 1% boric acid, 1-2% sodium citrate (dihydrate), 2-4% soda, 14-16% coconut fatty acids, 0.5% HEDP (1-hydroxyethane-(1,1-diphosphonic acid)), 0-0.4% PVP (polyvinylpyrrolidone), 0-0.05% optical brighteners, 0-0.001% dye, the rest demineralized water. Preferably, the dosage of the liquid detergent is between 4.5 and 6.0 grams per liter of washing liquor, for example, 4.7, 4.9 or 5.9 grams per liter of washing liquor. Washing is preferably performed in a pH range between pH 8 and pH 10.5, preferably between pH 8 and pH 9.

A preferred powdered detergent for such a washing system is composed as follows (all amounts in weight percent): 10% linear alkyl benzene sulfonate (sodium salt), 1.5% C12-C18 fatty alcohol sulfate (sodium salt), 2.0% C12-C18 fatty alcohol with 7 EO, 20% sodium carbonate, 6.5% sodium hydrogen carbonate, 4.0% amorphous sodium disilicate, 17% sodium carbonate peroxohydrate, 4.0% TAED, 3.0% polyacrylate, 1% carboxymethylcellulose, 1.0% phosphonate, 27% sodium sulfate, the rest: suds suppressors, optical brighteners, fragrances.

Preferably, the dosage of the powdered detergent is from 4.5 to 7.0 grams per liter of washing liquor, for example, and particularly preferably 4.7 grams per liter of washing liquor, or 5.5, 5.9 or 6.7 grams per liter of washing liquor. Washing is preferably performed in a pH range between pH 9 and pH 11.

The determination of the cleaning performance is preferably carried out at 40° C. using a liquid detergent as indicated above, wherein the washing operation is preferably performed for 70 minutes.

The whiteness, i.e. the lightening of the stains, as a measure of the cleaning performance, is preferably determined by optical measurement methods, preferably photometrically. A suitable device for this is, for example, the Minolta CM508d spectrometer. Typically, the devices used for the measurement must be previously calibrated with a white standard, preferably a supplied white standard.

Methods for determining protease activity are known to those skilled in the art of enzyme technology and are used routinely by said individuals. For example, such methods are disclosed in Tenside, volume 7 (1970), pages 125-132. Alternatively, the protease activity can be determined based on the release of the chromophore para-nitroaniline (pNA) from the substrate suc-L-Ala-L-Ala-L-Pro-L-Phe-p-nitroanilide (AAPF). The protease cleaves the substrate and releases pNA. The release of pNA causes an increase in absorbance at 410 nm, the course over time thereof being a measure of the enzymatic activity (see Del Mar et al., 1979). The measurement is performed at a temperature of 25*C, at pH 8.6, and a wavelength of 410 nm. The measurement time is 5 min, and the measurement interval 20s to 60s. The protease activity is usually indicated in protease units (PE). Suitable protease activities for example are about 2.2, about 5.5 or about 10 PE per mL washing liquor. However, the protease activity is not equal to zero.

The protein concentration can be determined using known methods, for example the BCA method (bicinchoninic acid; 2,2'-biquinolyl-4,4'-dicarboxylic acid) or the Biuret process (A. G. Gornall, C. S. Bardawill and M. M. David, J. Biol. Chem., 177 (1948), pages 751-766). The determination of the active protein concentration can be performed in this respect via a titration of the active centers using a suitable irreversible inhibitor (for proteases, for example, phenylmethylsulfonyl fluoride (PMSF)) and determination of the residual activity (see M. Bender et al., J. Am. Chem. Soc. 88, 24 (1966), pages 5890-5913).

Proteins can be combined into groups of immunologically related proteins by the reaction with an antiserum or a specific antibody. The members of such a group are characterized in that they have the same antigenic determinants recognized by an antibody. They are therefore so structurally similar to one another that they can be recognized by an antiserum or specific antibodies. Therefore, a further subject as contemplated herein is formed by proteases which are characterized in that they have at least one, and increasingly preferably two, three or four antigenic determinants identical to a protease as contemplated herein. Such proteases, due to their immunological matches, are structurally so similar to the proteases as contemplated herein that a similar function is also presumed.

In addition to the above-described amino acid modifications, proteases as contemplated herein can also comprise further amino acid modifications, in particular amino acid substitutions, insertions or deletions. Such proteases are further developed for example by targeted genetic modification, i.e. by mutagenesis, and are optimized for a specific purpose or with regard to specific characteristics (for example with regard to their catalytic activity, stability, etc.). Further, inventive nucleic acids can be introduced in recombination approaches and thus can be used to generate completely new proteases or other polypeptides.

The aim is to introduce targeted mutations into the known molecules, such as substitutions, insertions or deletions, for example in order to improve the cleaning performance of enzymes as contemplated herein. In particular, the surface charges and/or the isoelectric point of the molecules and thus their interactions with the substrate can be modified. For example, the net charge of the enzymes can be modified in order to thus influence the substrate binding in particular for use in detergents and cleaning agents. Alternatively or in addition, through one or more corresponding mutations, the stability of the protease can be increased, thereby improving its cleaning performance. Advantageous properties of individual mutations, for example single substitutions, can complement each other. A protease already optimized with respect to certain properties, for example with respect to its stability against surfactants and/or bleaching agents and/or other components, may therefore additionally be further developed within the scope as contemplated herein.

For the description of substitutions that concern exactly one amino acid position (amino acid exchanges), the following convention is applied: first, the amino acid naturally present is named in the form of the internationally accepted single-letter code, followed by the corresponding sequence position and finally the inserted amino acid. Several exchanges within the same polypeptide chain are separated by slashes. With insertions, additional amino acids are named according to the sequence position. With deletions, the missing amino acid is replaced by a symbol, such as a star or a stroke. For example, A95G describes the substitution of alanine at position 95 by glycine, A95AG describes the insertion of glycine after the amino acid alanine at position 95, and A95* describes the deletion of alanine at position 95. This nomenclature is known to those skilled in the art of enzyme technology.

Another subject as contemplated herein is therefore a protease which, in the numbering according to SEQ ID NO. 1, has the amino acid D at position 97 and/or the amino acid E at position 99 and is obtainable from a protease as contemplated herein as a starting molecule through a single or multiple conservative amino acid substitution. The term "conservative amino acid substitution" means the exchange (substitution) of an amino acid residue for another amino acid residue, wherein said exchange does not lead to a change in the polarity or charge at the position of the exchanged amino acid, for example, the exchange of a non-polar amino acid residue for another non-polar amino acid residue. Conservative amino acid substitutions within the scope as contemplated herein include, for example: G=A=S, I=V=L=M, D=E, N=Q, K=R, Y=F, S=T, G=A=I=V=L=M=Y=F=W=P=S=T.

Another subject of the present disclosure is a protease which, in the numbering according to SEQ ID NO 1, has the amino acid D at position 97 and/or the amino acid E at position 99 and which is obtainable as a starting molecule from a protease as contemplated herein by fragmentation, deletion, insertion or substitution mutagenesis and comprises an amino acid sequence which matches the starting molecule over a length of at least 50, 60, 70, 80, 90, 100, 110, 120, 130, 140, 150, 160, 170, 180, 190, 200, 210, 220, 230, 240 250, 260, 265 or 266 contiguous amino acids.

So it is for example possible to delete, at the termini or in the loops of the enzyme, individual amino acids, without thereby causing a loss or reduction in the proteolytic activity. Further, by such fragmentation, deletion, insertion or substitution mutagenesis, for example, the allergenicity of relevant enzymes can be lowered, and thus their overall usability can be improved. Advantageously, the enzymes maintain their proteolytic activity even after mutagenesis, i.e. their proteolytic activity corresponds at least to that of the starting enzyme. Even substitutions can exhibit advantageous effects. Both individual as well as a plurality of contiguous amino acids can be exchanged for other amino acids.

All of the above facts are also applicable to the method as contemplated herein for producing a protease. Therefore, a method as contemplated herein also comprises one or more of the following method steps:

(a) introducing a single or multiple conservative amino acid substitution into a protease as contemplated herein, wherein the amino acid D at position 97 and/or the amino acid E at position 99 in the numbering according to SEQ ID NO. 1 remain unchanged;

(b) modifying the amino acid sequence of a protease by fragmentation, deletion, insertion or substitution mutagenesis in such a way that the protease comprises an amino acid sequence which matches the starting molecule over a length of at least 50, 60, 70, 80, 90, 100, 110, 120 130, 140, 150, 160, 170, 180, 190, 200, 210, 220, 230, 240, 250, 260, 265 or 266 contiguous amino acids, wherein the amino acid D at position 97 and/or the amino acid E at position 99 in the numbering of SEQ ID NO. 1 remain unchanged.

All statements also apply to the method as contemplated herein.

A protease as contemplated herein may additionally be stabilized, in particular by one or more mutations, such as substitutions, or by coupling to a polymer. This is because increasing the stability during storage and/or during use, for example during the washing process, means that the enzymatic activity lasts longer and therefore the cleaning performance is improved. In principle, all stabilization possibilities as described in the prior art and/or appropriate can be considered. Preference is given to stabilizations be reached via mutations of the enzyme itself, since such stabilizations, after the recovery of the enzyme, require no further working steps. Sequence alterations suitable for this are known in the prior art. For example, proteases can thus be stabilized in that one or more tyrosine residues are exchanged for other amino acids.

Further possibilities of stabilization are, for example:
modifying the binding of metal ions, especially the calcium binding sites, for example by exchanging one or more of the amino acid(s) involved in calcium binding for one or more negatively charged amino acids and/or by introducing sequence changes in at least one of the sequences of the two amino acids arginine/glycine;
protecting against the influence of denaturing agents such as surfactants by mutations that cause a change in the amino acid sequence or at the surface of the protein;
exchanging amino acids which are close to the N-terminus for those which presumably come into contact with the rest of the molecule via non-covalent interactions and thus contribute to maintaining the globular structure.

Preferred embodiments are those in which the enzyme is stabilized in several ways, since a number of stabilizing mutations have an additive or synergistic effect.

Another subject as contemplated herein is a protease as described above, which is characterized in that it comprises at least one chemical modification. A protease having such a change is referred to as a derivative, i.e., the protease is derivatized.

Derivatives, in the sense of the present application, are understood accordingly to mean those proteins of which the pure amino acid chain has been chemically modified. Such derivatizations can be effected for example in vivo by the host cell expressing the protein. In this regard, couplings of low-molecular-weight compounds such as lipids or oligosaccharides are particularly emphasized. However, derivatizations can also be carried out in vitro, for example by the chemical conversion of a side chain of an amino acid or by covalent bonding of another compound to the protein. For example, the coupling of amines to carboxyl groups of an enzyme to alter the isoelectric point is possible. Such other compound may be another protein that is bound, for example via bifunctional chemical compounds, to a protein as contemplated herein. Likewise, derivatization is understood to mean covalent binding to a macromolecular carrier, or even a non-covalent inclusion in suitable macromolecular cage structures. Derivatizations can influence, for example, substrate specificity or the binding strength to the substrate or can cause transient blocking of the enzymic activity, if the attached substance is an inhibitor. This can be useful, for example, for the period of storage. Such modifications may also affect the stability or enzymatic activity. They can also serve to reduce the allergenicity and/or immunogenicity of the protein and thus increase, for example, its compatibility with skin. For example, couplings with macromolecular compounds such as polyethylene glycol improve the protein in terms of stability and/or skin compatibility.

Derivatives of a protein as contemplated herein can also be understood in the widest sense to mean preparations of these proteins. Depending on the recovery, processing or preparation, a protein may be associated with various other substances, for example, from the culture of the producing microorganisms. A protein may also have been mixed deliberately with other substances, for example to increase its storage stability.

Thus, all preparations of a protein as contemplated herein are therefore also included within the scope as contemplated herein. This is regardless of whether it actually produces this enzymatic activity in a particular preparation or not. This is because it may be desirable for it to have no, or only low activity during storage, and to only demonstrate its enzymatic function at the time of use. This may for example be controlled by suitable accompanying substances, for example.

In particular, the joint preparation of proteases with protease inhibitors is possible in this respect.

Regarding all of the above-described proteases or protease variants and/or derivatives, those that are particularly preferred in the context of the present disclosure are those of which the activity corresponds at least to that of the protease according to SEQ ID NO. 1 and/or SEQ ID NO. 3, and/or of which the cleaning performance corresponds at least to that of the protease according to SEQ ID NO. 1 and/or SEQ ID NO. 3, wherein the cleaning performance is determined in a washing system as described above.

Another subject as contemplated herein is a nucleic acid encoding for a protease as contemplated herein, as well as a vector containing such a nucleic acid, in particular a cloning vector or an expression vector.

These may be DNA or RNA molecules. They can be present as a single strand, as a single strand complementary to the aforesaid single strand, or as a double strand. Especially in the case of DNA molecules, the sequences of both complementary strands in all three possible reading frames have to be considered. It should also be borne in mind that different codons, i.e. base triplets, can code for the same amino acids, so that a certain amino acid sequence of several different nucleic acids may be coded. Because of this degeneracy of the genetic code, all nucleic acid sequences which can code one of the proteases as described above are included in this subject as contemplated herein. A person skilled in the art is able to determine these nucleic acid sequences with certainty, since, despite the degeneracy of the genetic code, individual codons are assigned to defined amino acids. Therefore, on the basis of an amino acid sequence, a person skilled in the art can determine nucleic acids coding for this amino acid sequence without difficulty.

Furthermore, one or more codons can be replaced by synonymous codons in nucleic acids as contemplated herein. This aspect particularly relates to the heterologous expression of the enzymes according to the disclosure. Any organism, for example a host cell of a production strain, thus has a specific codon use. The term 'codon use' is understood to mean the translation of the genetic code in amino acids by the respective organism. It can lead to bottlenecks in protein biosynthesis when the codons in the organism lying on the nucleic acid are facing a comparatively small number of charged tRNA molecules. Although coding for the same amino acid, this leads to the fact that, in the organism, a codon is translated less efficiently than a synonymous codon coding for the same amino acid. Due to the presence of a higher number of tRNA molecules for the synonymous codon, this can be translated efficiently in the organism.

Those skilled in the art are aware of methods that are nowadays well known, such as chemical synthesis or the polymerase chain reaction (PCR) in combination with molecular biology and/or protein-chemical standard methods, for producing the corresponding nucleic acids up to complete genes on the basis of known DNA and/or amino acid sequences. Such methods are known, for example, from Sambrook, J., Fritsch, E. F. and Maniatis, T. 2001. Molecular cloning: a laboratory manual, 3rd Edition Cold Spring Laboratory Press.

Vectors are understood in the sense of the present disclosure to mean elements consisting of nucleic acids which contain a nucleic acid as contemplated herein as characteristic nucleic acid region. They are able to establish this in a species or a cell line over several generations or cell divisions as a stable genetic element. Vectors are particularly useful for use in bacteria, especially plasmids, i.e. circular genetic elements. Within the scope of the present disclosure, a nucleic acid as contemplated herein is cloned into a vector. The vectors include, for example, those of which the origins are bacterial plasmids, viruses or bacteriophages, or predominantly synthetic vectors or plasmids with elements of various origins. With each of the additional genetic elements present, vectors are capable of establishing themselves in the respective host cells over several generations as stable units. They can be present extrachromosomally as independent units or can be integrated into a chromosome or chromosomal DNA.

Expression vectors include nucleic acid sequences that enable them to replicate in the host cells containing them, preferably microorganisms, particularly preferably bacteria, and to bring a contained nucleic acid to expression there. Expression is influenced in particular by the promoter or promoters that regulates/regulate transcription. In principle, the expression can be carried out by the natural promoter originally localized before the nucleic acid to be expressed, but also by a promoter of the host cell provided on the expression vector or by a modified or a completely different promoter of another organism or another host cell. In the present case, at least one promoter is provided for the expression of a nucleic acid as contemplated herein and is used for the expression thereof. Expression vectors may also be adjustable, for example by changing the culturing conditions or on reaching a certain cell density of the host cells containing them, or by addition of certain substances, in particular activators of gene expression. An example of such a substance is the galactose derivative isopropyl-B-D-thio-galactopyranoside (IPTG), which is used as an activator of the bacterial lactose operon (lac operon). In contrast to expression vectors, the nucleic acid contained is not expressed in cloning vectors.

Another subject as contemplated herein is a non-human host cell which contains a nucleic acid as contemplated herein or a vector as contemplated herein, or which contains a protease as contemplated herein, particularly one which secretes the protease into the medium surrounding the host cell. Preferably, a nucleic acid as contemplated herein or a vector as contemplated herein is transformed into a microorganism, which then represents a host cell as contemplated herein. Alternatively, individual components, i.e., nucleic acid fragments or parts of a nucleic acid as contemplated herein can be introduced into a host cell so that the resulting host cell contains a nucleic acid as contemplated herein or a vector as contemplated herein. This procedure is particularly suitable when the host cell already contains one or more components of a nucleic acid as contemplated herein or a vector as contemplated herein and the other components are then supplemented accordingly. Methods for transformation of cells are well established in the prior art and are known to those skilled in the art. Suitable host cells are in principle all cells, that is to say prokaryotic or eukaryotic cells. Preferred host cells can be genetically handled in an advantageous manner, which for example concerns the transformation with the nucleic acid or the vector and its stable establishment, for example unicellular fungi or bacteria. Moreover, preferred host cells are distinguished by good microbiological and biotechnological manageability. This concerns, for example, ease of culture, high growth rates, low demands on fermentation media, and good production and secretion rates for foreign proteins. Preferred host cells as contemplated herein secrete the (transgenic) expressed protein into the medium surrounding the host cells. Further, the proteases may be modified from the cells producing them after their production, for example by attachment of sugar molecules, formylation, amination, etc. Such post-translational modifications can functionally affect the protease.

Other preferred embodiments are those host cells of which the activity can be regulated due to genetic regulatory elements which are provided for example on the vector, but which also may be present from the outset in these cells.

For example, by controlled addition of chemical compounds which act as activators, by changing the culturing conditions or on reaching a certain cell density, these host cells can be induced to express. This allows economical production of proteins as contemplated herein. An example of such a compound IPTG as described above.

Preferred host cells are prokaryotic or bacterial cells. Bacteria are characterized by short generation times and low demands on the culturing conditions. This enables cost-effective culture methods or production methods to become established. In addition, a person skilled in the art has a wealth of experience of bacteria in fermentation technology. For a specific production, gram-negative or gram-positive bacteria may be suitable for a wide variety of reasons to be determined by way of experiment in each individual case, such as nutrient sources, product formation rate, time required, etc.

In the case of gram-negative bacteria such as *Escherichia coli*, a variety of proteins in the periplasmic space are secreted, i.e. into the compartment between the two membranes enclosing the cells. This may be advantageous for particular applications. Furthermore, gram-negative bacteria can also be designed so that they not only discharge the expressed proteins into the periplasmic space, but into the medium surrounding the bacterium. By contrast, gram-positive bacteria such as bacilli or actinomycetes or other representatives of actinomycetales possess no external membrane, so that secreted proteins are immediately delivered into the medium surrounding the bacteria, usually the nutrient medium, from which the expressed proteins can be purified. They can be isolated directly from the medium or further processed. In addition, gram-positive bacteria are related to most source organisms for industrially important enzymes or are identical thereto and usually themselves form comparable enzymes so that they have a similar codon use and their protein synthesis apparatus is appropriately aligned naturally.

Inventive host cells may be modified to the culture conditions in terms of their requirements, may have other or additional selection markers, or may even express other or additional proteins. In particular, they may also be host cells which transgenically express a number of proteins or enzymes.

The present disclosure is in principle applicable to all microorganisms, especially all fermentable microorganisms, particularly preferably those of the genus *Bacillus*, and results in the possibility to produce proteins as contemplated herein by the use of such microorganisms. Such microorganisms then constitute host cells within the meaning as contemplated herein.

In a further embodiment as contemplated herein the host cell is characterized in that it is a bacterium, preferably one that is selected from the group of genera *Escherichia, Klebsiella, Bacillus, Staphylococcus, Corynebacterium, Arthrobacter, Streptomyces, Stenotrophomonas* and *Pseudomonas*, more preferably one that is selected from the group consisting of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*.

The host cell, however, may also be a eukaryotic cell, which is characterized in that it possesses a nucleus. A further subject as contemplated herein therefore provides a host cell which is characterized in that it possesses a nucleus. In contrast to prokaryotic cells, eukaryotic cells are capable of modifying the protein formed post-translationally. Examples are fungi such as actinomycetes or yeasts such as *Saccharomyces* or *Kluyveromyces*. This may be particularly advantageous for example if the proteins are to experience specific modifications in relation to their synthesis. The modifications which eukaryotic systems carry out, particularly in connection with the protein synthesis, include for example the binding of low-molecular-weight compounds such as membrane anchors or oligosaccharides.

Oligosaccharide modifications may for example be desirable to reduce the allergenicity of an expressed protein. Co-expression with the enzymes naturally formed by such cells, such as cellulases or lipases, may also be advantageous. Further, thermophilic fungal expression systems can be particularly suitable for expressing thermally resistant proteins or variants, for example.

The host cells as contemplated herein are cultured and fermented in a conventional manner, for example in batch or continuous systems. In the first case a suitable nutrient medium is inoculated with the host cells and the product is harvested from the medium after a period of time to be determined experimentally. Continuous fermentations are characterized by reaching a steady state, in which, over a comparatively long time, cells partially die but also grow again, and the protein produced can be removed from the medium at the same time.

Host cells as contemplated herein are preferably used to produce proteases as contemplated herein. Another subject as contemplated herein is therefore a method for producing a protease, comprising the steps of
a) culturing a host cell as contemplated herein
b) isolating the protease from the culture medium or from the host cell.

This subject as contemplated herein preferably comprises fermentation processes. Fermentation processes are known per se from the prior art and represent the actual industrial production step, usually followed by a suitable purification method of the product produced, for example the protease as contemplated herein. All fermentation processes which are based on an appropriate method for producing a protease as contemplated herein constitute embodiments of this subject as contemplated herein.

Fermentation processes which are characterized in that the fermentation is carried out with a supply strategy are especially considered. Here, the media components that are consumed by the ongoing culture are fed.

This can result in significant growth in both cell density and cell mass or dry mass and/or especially in the activity of the protease of interest. Further, the fermentation can also be designed so that undesirable metabolic products can be filtered out or neutralized by the addition of buffers or matching counter ions.

The protease produced can be harvested from the fermentation medium. Such a fermentation process is preferred compared to the isolation of the protease from the host cell, i.e., a product preparation from the cell mass (dry mass) is preferred, but requires the provision of suitable host cells or of one or more suitable secretion markers or mechanisms and/or transport systems, so that the host cells secrete the protease into the fermentation medium. Without secretion, alternatively, the protease can be isolated from the host cell, i.e. can be purified from the cell mass, for example by precipitation with ammonium sulfate or ethanol, or by chromatographic purification.

All facts set forth above may be combined with methods to produce proteases as contemplated herein.

Another subject as contemplated herein is an agent which is characterized in that it contains a modified protease as contemplated herein as described above. Preferably, the agent is a detergent or cleaning agent. Since modified proteases as contemplated herein have advantageous cleaning performances in particular on stains containing blood and whole egg, the agents are suitable and advantageous in particular for the removal of such stains.

This subject as contemplated herein includes all conceivable detergent or cleaning agent types, both concentrates and agents to be used without dilution, for use on a commercial scale, in washing machines or in the case of hand washing or cleaning. These include, for example, washing products for textiles, carpets or natural fibers, for which the term 'detergent' is used. These include also dishwashing products for dishwashers or manual dishwashing products, or cleaning products for hard surfaces, such as metal, glass, porcelain, ceramics, tiles, stone, painted surfaces, plastics, wood or leather, for which the term 'cleaning agent' is used, i.e. besides manual and automatic dishwashing products, for example also abrasives, glass cleaning agents, toilet fresheners, etc. The detergents and cleaning agents within the scope as contemplated herein further include washing aids which, in the case of the washing of textiles by hand or machine, are added in a metered manner to the actual washing product to achieve a further effect. Further, detergents and cleaning agents within the scope as contemplated herein also include textile pre-treatment and post-treatment products, i.e., those agents with which the laundry article is contacted before the actual washing operation, for example in order to dissolve stubborn dirt, and also those agents that provide the item to be washed with further desirable properties in a step subsequent to the actual washing of the laundry, such as a pleasant feel, crease resistance, or low static charge. The latter agents include softeners, among others.

The proportion by weight, based on active protein, of the protease as contemplated herein in the total weight of the inventive detergent or cleaning agent is preferably 0.005 to 1.0 wt. %, preferably 0.01 to 0.5 wt. %, and in particular 0.02 to 0.2 wt. %. The protein concentration can be determined using known methods, for example the BCA method (bicinchoninic acid; 2,2'-biquinolyl-4,4'-dicarboxylic acid) or the biuret process (A. G. Gornall, C. S. Bardawill and M. M. David, J. Biol. Chem., 177 (1948), pages 751-766). The determination of the active protein concentration is carried out in this respect via a titration of the active centers using a suitable irreversible inhibitor (for proteases, for example, phenylmethylsulfonyl fluoride (PMSF)), and determination of the residual activity (see M. Bender et al., J. Am. Chem. Soc. 88, 24 (1966), pages 5890-5913).

The detergents or cleaning agents as contemplated herein can contain further enzymes. For example lipases or cutinases can be used as further enzymes, in particular because of their triglyceride-cleaving activities, but also to produce peracids from suitable precursors in situ. These include, for example, the lipases originally obtainable or further developed from *Humicola lanuginose* (*Thermomyces lanuginosus*), in particular those with the D96L amino acid substitution. These include, for example, the lipases originally obtainable or further developed from *Humicola lanuginosa* (*Thermomyces lanuginosus*), in particular those with one or more of the following amino acid substitutions starting from the above lipase in the positions D96L, T213R and/or N233R., particularly preferably T213R and N233R. Furthermore, the cutinases which were originally isolated from *Fusarium solani pisi* and *Humicola insolens* can be used, for example. Lipases or cutinases of which the starting enzymes were originally isolated from *Pseudomonas mendocina* and *Fusarium solanii* can also be used.

The agents as contemplated herein can also contain cellulases or hemicellulases such as mannanases, xanthans, pectins (=pectinases), pectin esterases, pectatlyases, xyloglucanases (=xylanases), pullulanases or B-glucanases.

To increase the bleaching action, oxidoreductases, for example oxidases, oxygenases, catalases, peroxidases, such as halo-, chloro-, bromo-, lignin, glucose or manganese peroxidases, dioxygenases or laccases (phenol oxidases, polyphenol oxidases) may be used as contemplated herein. Advantageously, preferably organic compounds, particularly preferably aromatic compounds, which interact with the enzymes are additionally added to enhance the activity of the oxidoreductases concerned (enhancers), or to ensure the flow of electrons in the case of strongly different redox potentials between the oxidizing enzymes and the stains (mediators).

Amylases can also be used as further enzymes. Synonymous terms for amylases may be used, for example, 1,4-alpha-D-glucan glucanohydrolase or glycogenase. As contemplated herein, preferred amylases are a-amylases. What is key for whether an enzyme is an α-amylase as contemplated herein is its ability to hydrolyze a(1-4)-glycosidic bonds in the amylose of the starch.

Exemplary amylases are the α-amylases from *Bacillus licheniformis, Bacillus amyloliquefaciens* or from *Bacillus stearothermophilus* and especially their improved developments for use in detergents or cleaning agents. The enzyme from *Bacillus licheniformis* is available from the company Novozymes under the name Termamyl® and from the company Danisco/Genencor under the name Purastar®ST.

Development products of this α-amylase are available from the company Novozymes under the trade names Duramyl® and Termamy®ultra, from the company Danisco/Genencor under the name Purastar®OxAm, and from the company Daiwa Seiko Inc., Tokyo, Japan, as Keistase®. The α-amylase from *Bacillus amyloliquefaciens* is marketed by the company Novozymes under the name BAN®, and variants derived from the α-amylase from *Bacillus stearothermophilus* are marketed under the names BSG® and Novamyl®, also from the company Novozymes. Furthermore, the α-amylase from *Bacillus* sp. A 7-7 (DSM 12368) and the cyclodextrin glucanotransferase (CGTase) from *Bacillus agaradherens* (DSM 9948) should be emphasized for this purpose. Fusion products of all the molecules mentioned can also be used. Moreover, the developments of α-amylase from *Aspergillus niger* and *A. oryzae* available under the trade names Fungamyl® from the company Novozymes are suitable. Further commercial products that can be used advantageously are for example the Amylase-LT® and Stainzyme® or Stainzyme Ultra® or Stainzyme Plus®, the latter also from the company Novozymes. Variants of this enzyme also obtainable by point mutations can be used as contemplated herein. Particularly preferred amylases are disclosed in the international laid-open applications WO 00/60060, WO 03/002711, WO 03/054177 and WO07/079938, to the disclosure of which reference is therefore expressly, or the disclosure of which in this regard is therefore expressly incorporated into the present patent application.

The proportion by weight, based on active protein, of the further enzyme in the total weight of preferred detergents or cleaning agents is preferably from 0.0005 to 1.0 wt. %, preferably from 0.001 to 0.5 wt. %, and in particular 0.002 to 0.2 by wt. %.

The detergents or cleaning agents may contain cleaning-active substances in addition to the ingredients described above, wherein substances from the group of surfactants, builders, polymers, glass corrosion inhibitors, corrosion inhibitors, fragrances, and perfume carriers are preferred. These preferred ingredients are described in more detail below.

A preferred component of the detergent or cleaning agent as contemplated herein is constituted by the non-ionic surfactants, wherein non-ionic surfactants of general formula $R^1$—CH(OH)CH$_2$O-(AO)$_w$-(A'O)$_x$-(A"O)$_y$—('"O)$_z$—$R^2$, in which
  $R^1$ is a straight-chain or branched, saturated or mono- or polyunsaturated $C_{6-24}$ alkyl or alkenyl residue;
  $R^2$ stands for a linear or branched hydrocarbon functional group having 2 to 26 carbon atoms;
  A, A', A" and A'" independently of one another stand for a functional group from —CH$_2$CH$_2$, —CH$_2$CH$_2$—CH$_2$, —CH$_2$—CH(CH$_3$), CH$_2$—CH$_2$—CH$_2$—CH$_2$, CH$_2$—CH(CH$_3$)—CH$_2$—, —CH$_2$—CH(CH$_2$CH$_3$),
  w, x, y and z are values between 0.5 and 120, wherein x, y and/or z can also be 0, are preferred.

By the addition of the aforementioned non-ionic surfactants of the general formula R1-CH(OH)CH2O-(AO)w-(A'O)x-(A"O)y-('"O)z-R2, hereinafter also referred to as "hydroxy mixed ethers," the cleaning performance of enzyme-containing preparations as contemplated herein can be significantly improved both in comparison to surfactant-free systems as well as in comparison to systems that contain alternative non-ionic surfactants, for example from the group of polyalkoxylated fatty alcohols.

Through the use of these non-ionic surfactants having one or more free hydroxyl groups at one or both terminal alkyl functional groups, the stability of the enzymes contained in the detergent or cleaning agent preparations as contemplated herein can be significantly improved.

Particularly preferred are terminal-group-capped poly (oxyalkylated) non-ionic surfactants which, according to the formula R1O[CH2CH2O]xCH2CH(OH)R2, in addition to a group R1, which stands for linear or branched, saturated or unsaturated, aliphatic or aromatic hydrocarbon functional groups having 2 to 30 carbon atoms, preferably having 4 to 22 carbon atoms, further comprise a linear or branched, saturated or unsaturated, aliphatic or aromatic hydrocarbon functional group R2 having 1 to 30 carbon atoms, wherein x stands for values between 1 and 90, preferably for values between 30 and 80, and in particular for values between 30 and 60.

Particularly preferred are surfactants of the formula R1O[CH2CH(CH3)O]x[CH2CH2O]yCH2CH(OH)R2, in which R1 is a linear or branched aliphatic hydrocarbon functional group having 4 to 18 carbon atoms or mixtures thereof, R2 is a linear or branched hydrocarbon functional group having from 2 to 26 carbon atoms or mixtures thereof, and x denotes values between 0.5 and 1.5, and y stands for a value of at least 15.

The group of these non-ionic surfactants includes, for example, the $C_{2-26}$ fatty alcohol —(PO)$_1$-(EO)$_{15-40}$-2-hydroxyalkyl ethers, in particular also the $C_{8-10}$ fatty alcohol —(PO)$_1$(EO)$_{22}$-2-hydroxydecyl ethers.

Especially preferred are also terminal-group-capped poly (oxyalkylated) non-ionic surfactants of the formula $R^1O[CH_2CH_2O]_x[CH_2CH(R^3)O]_yCH_2CH(OH)R^2$, in which $R^1$ and $R^2$ independently of one another stand for a linear or branched, saturated or mono- or polyunsaturated hydrocarbon functional group with 2 to 26 carbon atoms, $R^3$ is independently selected from —CH$_3$, —CH$_2$CH$_3$, —CH$_2$CH$_2$—CH$_3$, —CH(CH$_3$)$_2$, but preferably stands for —CH$_3$, and x and y independently stand for values between 1 and 32, wherein non-ionic surfactants with $R^3$=—CH$_3$ and values for x from 15 to 32 and y of 0.5 and 1.5 are very particularly preferred.

Other non-ionic surfactants that can be used with preference are the terminal-group-capped poly(oxyalkylated) non-ionic surfactants of the formula R1O[CH2CH(R3)O]x[CH2]kCH(OH)[CH2]jOR2, in which R1 and R2 stand for linear or branched, saturated or unsaturated, aliphatic or aromatic hydrocarbon functional groups having 1 to 30 carbon atoms, R3 stands for a methyl, ethyl, n-propyl, iso-propyl, n-butyl, 2-butyl or 2-methyl-2-butyl group, x stands for values between 1 and 30, k and j stand for values between 1 and 12, preferably between 1 and 5. If the value x is ≥2, each R3 in the above-mentioned formula R1O[CH2CH(R3)O]x[CH2]kCH(OH)[CH2]jOR2 can be different. R1 and R2 are preferably linear or branched, saturated or unsaturated, aliphatic or aromatic hydrocarbon functional groups having 6 to 22 carbon atoms, wherein groups having 8 to 18 C atoms are particularly preferred. For the group R3, H, —CH3 or —CH2CH3 are particularly preferred. Particularly preferred values for x are in the range of 1 to 20, in particular 6 to 15.

As described above, each R3 may be different in the above formula, if x≥2. This allows the alkylene oxide unit within the square brackets to be varied. For example, if x is 3, the group R3 can be selected to form ethylene oxide units (R3=H) or propylene oxide units (R3=CH3), which can be joined together in any sequence, for example (EO)(PO)(EO), (EO)(EO)(PO), (EO)(EO) (EO), (PO)(EO)(PO), (PO)(PO)(EO) and (PO)(PO)(PO). The value 3 for x has been selected here by way of example and may easily be higher, wherein the variation increases with rising values of x and, for example, includes a large number of (EO) groups combined with a small number of (PO) groups, or vice versa.

Particularly preferred terminal-group-capped poly(oxyalkylated) alcohols of the above-mentioned formula have values of k=1 and j=1, so that the above formula is simplified to R1O[CH2CH(R3)O]x[CH2]CH(OH)CH2OR2. In this formula, R1, R2 and R3 are as defined above and x stands for numbers from 1 to 30, preferably from 1 to 20 and in particular from 6 to 18. Particularly preferred surfactants are those in which the groups R1 and R2 have 9 to 14 C atoms, R3 stands for H and x assumes values of 6 to 15.

Lastly, the non-ionic surfactants of the general formula $R^1$—CH(OH)CH$_2$O-(AO)$_w$—$R^2$ have proven to be particularly effective, in which $R^1$ stands for a straight-chain or branched, saturated or mono- or polyunsaturated $C_{6-24}$ alkyl or -alkenyl residue:

$R^2$ stands for a linear or branched hydrocarbon functional group having 2 to 26 carbon atoms:

A stands for a group from CH$_2$CH$_2$, —CH$_2$CH$_2$—CH$_2$, —CH$_2$—CH(CH$_3$), and w stands for values between 1 and 120, preferably 10 to 80, particularly 20 to 40.

The group of these non-ionic surfactants includes, for example, the C4-22 fatty alcohol (EO)$_{10-80}$-2-hydroxyalkl ethers, in particular the $C_{8-12}$ fatty alcohol (EO)$_{22}$-2-hydroxydecyl ethers and the C4-22 fatty alcohol (EO)$_{40-80}$-2-hydroxyalkyl ethers.

Preferred detergents or cleaning agents are characterized in that the detergent or cleaning agent contains at least one non-ionic surfactant, preferably a non-ionic surfactant from the group of hydroxy mixed ethers, wherein the proportion by weight of the non-ionic surfactant in the total weight of the detergent or cleaning agent is preferably from 0.2 to 10 wt. %, preferably from 0.4 to 7.0 wt. % and preferably from 0.6 to 6.0 wt. %.

Preferred inventive detergents or cleaning agents for use in automatic dishwashing processes contain, in addition to the non-ionic surfactants described above, further surfactants, in particular amphoteric surfactants. The proportion of anionic surfactants in the total weight of these detergents or cleaning agents, however, is preferably limited. Thus, preferred automatic dishwashing products are characterized in that they contain, in relation to their total weight, less than 5.0 wt. %. preferably less than 3.0 wt. %, particularly preferably less than 2.0 wt. % of anionic surfactant. Here, the use of anionic surfactants in a larger amount is dispensed with, in particular in order to avoid an excessive foaming.

Another preferred constituent of the inventive detergents or cleaning agents are complexing agents. Particularly preferred complexing agents are the phosphonates. The complexing phosphonates comprise, in addition to 1-hydroxyethane-1,1-diphosphonic acid, also a number of different compounds such as diethylenetriaminepenta (methylene phosphonic acid) (DTPMP). In this application hydroxyalkane- and aminoalkane phosphonates are preferred in particular. Among the hydroxyalkane phosphonates, 1-hydroxyethane-1,1-diphosphonate (HEDP) is of particular importance as co-builder. It is preferably used as sodium salt, wherein the disodium salt reacts in a neutral manner and the tetrasodium salt reacts in an alkaline manner (pH 9). Aminoalkane phosphonates are preferably ethylenediamine tetra(methylene phosphonic acid) (EDTMP), diethylenetriaminepenta(methylene phosphonic acid) (DTPMP) and their higher homologs. They are preferably used in the form of the neutrally reacting sodium salts, for example as a hexasodium salt of EDTMP or as the hepta and octa sodium salt of DTPMP. From the class of phosphonates, HEDP is preferably used as builder. The aminoalkane phosphonates additionally have a pronounced heavy metal binding capacity. Accordingly, in particular if the agents also contain bleaches, it can be preferred to use aminoalkane phosphonates, in particular DTPMP, or mixtures of said phosphonates.

A preferred detergent or cleaning agent within the scope of this application contains one or more phosphonate(s) selected from the group a) aminotrimethylene phosphonic acid (ATMP) and/or salts thereof;

b) ethylenediamine tetra(methylene phosphonic acid) (EDTMP) and/or salts thereof;

c) diethylenetriaminepenta(methylene phosphonic acid) (DTPMP), and/or salts thereof;

d) 1-hydroxyethane-1,1-diphosphonic acid (HEDP) and/or salts thereof;

e) 2-phosphonobutane-1,2,4-tricarboxylic acid (PBTC) and/or salts thereof;

f) hexamethylenediamine tetra(methylene phosphonic acid) (HDTMP), and/or salts thereof;

g) nitrilotri(methylene phosphonic acid) (NTMP) and/or salts thereof.

Detergents or cleaning agents which are particularly preferred are those which contain 1-hydroxyethane-1,1-diphosphonic acid (HEDP) or diethylenetriaminepenta(methylene phosphonic acid) (DTPMP) as phosphonates. Of course, the detergents or cleaning agents as contemplated herein can contain two or more different phosphonates. Preferred detergents or cleaning agents as contemplated herein are characterized in that the detergent or cleaning agent contains at least one complexing agent from the group of phosphonates, preferably 1-hydroxyethane-1,1-diphosphonate, wherein the proportion by weight of the phosphonate in the total weight of the detergent or cleaning agent is preferably from 0.1 to 8.0 wt. %, preferably from 0.2 and 5.0 wt. % and in particular from 0.5 and 3.0 wt. %.

The detergents or cleaning agents as contemplated herein also preferably contain builders. The builders here include, in particular, silicates, aluminum silicates (particularly zeolites), salts of organic di- and polycarboxylic acids, and mixtures of these substances, preferably water-soluble builder substance carbonates, organic cobuilders, preferably water-soluble builders, and, where there are no ecological objections to their use, the phosphates.

Among the multitude of commercially available phosphates, the alkali metal phosphates, with particular preference pentasodium phosphate, Na5P3O10 (sodium tripolyphosphate) or pentapotassium phosphate K5P3O10 (potassium tripolyphosphate) for the agents as contemplated herein are the most important. If, within the scope of the present application, phosphates are used as cleaning-active substances used in the detergents or cleaning agents, preferred agents contain this/these phosphate(s), preferably pentapotassium triphosphate, wherein the proportion by weight of the phosphate in the total weight of the detergent or cleaning agent is preferably 5.0 and 40 wt. %, preferably 10 and 30 wt. %, and in particular 12 and 25 wt. %.

In an embodiment that is particularly preferred as contemplated herein the use of phosphates (including polyphosphates) is largely or completely dispensed with. The agent in this embodiment contains preferably less than 5 wt. %, particularly preferably less than 3 wt. %, in particular less than 1 wt. % of phosphate(s). Particularly preferably, the agent in this embodiment is completely phosphate-free, i.e., the agents contain less than 0.1 wt. % phosphate(s).

Examples of organic cobuilders are in particular polycarboxylates/polycarboxylic acids, polymeric polycarboxylates, aspartic acid, polyacetals, dextrins, other organic cobuilders, and phosphonates. These classes of substance are described below.

Organic builders that are suitable as contemplated herein are, for example, the polycarboxylic acids (polycarboxylates) usable in the form of their sodium salts, wherein polycarboxylic acids are understood to be carboxylic acids carrying more than one, in particular two to eight acid functions, preferably two to six, in particular two, three, four or five acid functions in the entire molecule. What are preferred as polycarboxylic acids are thus dicarboxylic acids, tricarboxylic acids, tetracarboxylic acids and pentacarboxylic acids, especially di-, tri- and tetracarboxylic acids. Here, the polycarboxylic acids can also carry other functional groups, such as hydroxyl or amino groups. For example, these are citric acid, adipic acid, succinic acid, glutaric acid, malic acid, tartaric acid, maleic acid, fumaric acid, sugar acids (preferably aldaric acids, for example galactaric acid and glucaric acid), amino carboxylic acids, particularly amino dicarboxylic acids, aminotricarboxylic acids, aminotetracarboxylic acids, such as nitrilotriacetic acid (NTA), glutamine-N,N-diacetic (also known as N,N-bis(carboxymethyl)-L-glutamic acid or GLDA), methylglycine diacetic acid (MGDA)) and derivatives thereof and mixtures thereof. Preferred salts are the salts of polycarboxylic acids such as citric acid, adipic acid, succinic acid, glutaric acid, tartaric acid, GLDA, MGDA and mixtures thereof.

Other suitable organic builders are polymeric polycarboxylates (organic polymers with a plurality of (in particular more than ten) carboxylate functions in the macromolecule), polyaspartate, polyacetals and dextrins.

The molar masses given for polymeric polycarboxylates are, for the purposes of this specification, weight-average molar masses Mw of the particular acid form which, fundamentally, were determined by gel permeation chromatography (GPC) using a UV detector. The measurement was made against an external polyacrylic acid standard, which delivers realistic molecular weight values because of its structural similarity to the polymers under investigation. These figures differ significantly from the molecular weights where polystyrene sulfonic acids are used as standard. The molar masses measured against polystyrene sulfonic acids are generally significantly higher than the molar masses mentioned in this specification.

Particularly suitable polymers are polyacrylates which preferably have a molecular mass of from 2,000 to 20,000 g/mol. Owing to their superior solubility, the short-chain polyacrylates having molar masses of from 2,000 to 10,000 g/mol, and particularly preferably from 3000 to 5000 g/mol, may be preferred in turn from this group.

Also suitable are copolymeric polycarboxylates, especially those of acrylic acid with methacrylic acid and of acrylic or methacrylic acid with maleic acid. Copolymers of acrylic acid with maleic acid containing from 50 to 90 wt. % acrylic acid and from 50 to 10 wt. % maleic acid have proven to be particularly suitable. Their relative molecular mass, based on free acids, is generally from 2,000 to 70,000 g/mol, preferably from 20,000 to 50,000 g/mol and in particular from 30,000 to 40,000 g/mol.

Oxydisuccinates and other derivatives of disuccinates, preferably ethylenediamine disuccinate, are further suitable cobuilders. Ethylenediamine-N,N'-disuccinate (EDDS) is preferably used in the form of its sodium or magnesium salts. Also preferred in this context are glycerol disuccinates and glycerol trisuccinates.

To improve the cleaning performance and/or to adjust the viscosity, preferred detergents or cleaning agents contain at least one hydrophobically modified polymer, preferably a hydrophobically modified carboxylic acid group-containing polymer, wherein the proportion by weight of the hydrophobically modified polymer in the total weight of the detergent or cleaning agent is preferably from 0.1 to 10 wt. %, preferably between 0.2 and 8.0 wt. %, and in particular from 0.4 to 6.0 wt. %.

In addition to the builders described above, cleaning-active polymers can be contained in the detergent or cleaning agent. The proportion by weight of the cleaning-active polymers in the total weight of the automatic detergent or cleaning agent as contemplated herein is preferably 0.1 to 20 wt. %, preferably from 1.0 to 15 wt. %, and in particular from 2.0 to 12 wt. %.

Sulfonic acid group-containing polymers, in particular from the group of copolymeric polysulfonates, are preferably used as cleaning-active polymers. These copolymeric polysulfonates contain, in addition to sulfonic acid group-containing monomer(s), at least one monomer from the group of unsaturated carboxylic acids.

Unsaturated carboxylic acids of the formula $R1(R2)C=C(R3)COOH$, in which R1 to R3 independently of one another stand for —H, —CH3, a straight-chain or branched saturated alkyl functional group having 2 to 12 carbon atoms, a straight-chain or branched, mono- or polyunsaturated alkenyl residue having 2 to 12 carbon atoms, alkyl or alkenyl residues substituted with —OH or —COOH as defined as above, or for —COOH, or —COOR4, wherein R4 is a saturated or unsaturated, straight-chain or branched hydrocarbon functional group having from 1 to 12 carbon atoms, is/are used with preference as unsaturated carboxylic acid(s).

Especially preferred unsaturated carboxylic acids are acrylic acid, methacrylic acid, ethacrylic acid, a-chloroacrylic acid, a-cyanoacrylic acid, crotonic acid, a-phenyl acrylic acid, maleic acid, maleic anhydride, fumaric acid, itaconic acid, citraconic acid, methylenemalonic acid, sorbic acid, cinnamic acid or mixtures thereof. Of course, the unsaturated dicarboxylic acids can also be used.

Among the monomers containing sulfonic acid groups, those of the formula $R5(R6)C=C(R7)-X-SO3H$ are preferred, in which R5 to R7 independently of one another stand for —H, —CH$_3$, a straight-chain or branched saturated alkyl functional group having 2 to 12 carbon atoms, a straight-chain or branched, mono- or polyunsaturated alkenyl residue having 2 to 12 carbon atoms, alkyl or alkenyl residues substituted with —NH2, —OH or —COOH, or for —COOH or —COOR4, wherein R4 is a saturated or unsaturated, straight-chain or branched hydrocarbon functional group having 1 to 12 carbon atoms, and X is an optionally present spacer group which is selected from —(CH2)n- with n=0 to 4, —COO—(CH2)k- with k=1 to 6, —C(O)—NH—C(CH3)2-, —C(O)—NH—C(CH3)2-CH2- and —C(O)—NH—CH(CH2CH3)-.

Among these monomers, those of the formulas H2C=CH—X—SO3H, H2C=C(CH3)-X—SO3H and HO3S-X—(R6)C=C(R7)-X—SO3H, in which R6 and R7 independently of one another are selected from —H, —CH3, —CH2CH3, —CH2CH2CH3, —CH(CH3)2 and X stands for an optionally present spacer group which is selected from —(CH2)n- with n=0 to 4, —COO—(CH2)k- with k=1 to 6, —C(O)—NH—C(CH3)2-, —C(O)—NH—C(CH3)2-CH2- and —C(O)—NH—CH(CH2CH3)-.

Particularly preferred sulfonic acid group-containing monomers here are 1-acrylamido-1-propane sulfonic acid, 2-acrylamido-2-propane sulfonic acid, 2-acrylamido-2-methyl-1-propane sulfonic acid, 2-methacrylamido-2-methyl-1-propane sulfonic acid, 3-methacrylamido-2-hydroxy-propane sulfonic acid, allylsulfonic acid, methallylsulfonic acid, allyloxybenzene sulfonic acid, methallyloxybenzene sulfonic acid, 2-hydroxy-3-(2-propenyloxy)propane sulfonic acid, 2-methyl-2-propenl-sulfonic acid, styrenesulfonic acid, vinylsulfonic acid, 3-sulfopropyl acrylate, 3-sulfopropyl-methacrylate, sulfomethacrylamide, sulfomethylmethacrylamide and mixtures of said acids or their water-soluble salts.

In the polymer, the sulfonic acid groups can be wholly or partly present in neutralized form. The use of partially or completely neutralized sulfonic acid group-containing copolymer is preferable as contemplated herein.

The molar mass of the sulfo copolymers used as contemplated herein preferably can be varied to adjust the properties of the polymers to the desired application. Preferred automatic dishwashing products are characterized in that the copolymers have molar masses of 2,000-200,000 gmol-1, preferably of 4,000-25,000 gmol-1, and in particular 5,000-15,000 gmol-1.

In a further preferred embodiment, the copolymers comprise, in addition to carboxyl group-containing monomer and sulfonic acid group-containing monomer, also at least one non-ionic, preferably hydrophobic monomer. By using these hydrophobically modified polymers, in particular the rinsing performance of automatic dishwashing products as contemplated herein could be improved.

Detergents or cleaning agents containing a copolymer comprising i) carboxylic acid group-containing monomer(s)
ii) sulfonic acid group-containing monomer(s)
iii) non-ionic monomer(s)

are preferred as contemplated herein. Through the use of these terpolymers, the rinsing performance of automatic dishwashing products as contemplated herein could be improved compared to comparable dishwashing products containing sulfopolymers without the addition of non-ionic monomers.

Suitable non-ionic monomers are preferably monomers of the formula R1(R2)C=C(R3)-X—R4, in which R1 to R3 independently of one another stand for —H, —CH3 or —C2H5, X stands for an optionally present spacer group which is selected from —CH2-, —C(O)O— and —C(O)—NH—, and R4 stands for a straight-chain or branched saturated alkyl functional group having 2 to 22 carbon atoms or for an unsaturated, preferably aromatic group having 6 to 22 carbon atoms.

Particularly preferred non-ionic monomers are butene, isobutene, pentene, 3-methylbutene, 2-methylbutene, cyclopentene, hexene, hexene-1,2-methlypentene-1,3-methlypentene-1, cyclohexene, methylcyclopentene, cycloheptene, methylcyclohexene, 2,4,4-trimethylpentene-1,2,4,4-trimethylpentene-2,2,3-dimethylhexene-1,2,4-dimethylhexene-1, 2,5-dimethlhexene- 1, 3,5-dimethylhexene-1,4,4-dimehtylhexane-1, ethylcyclohexyne, 1-octene, α-olefins having 10 or more carbon atoms such as 1-decene, 1-dodecene, 1-hexadecene, 1-octadecene and C22 α-olefin, 2-styrene, a-methylstyrene, 3-methylstyrene, 4-propylstyrene, 4-cyclohexylstyrene, 4-dodecylstyrene, 2-ethyl-4-benzylstyrene, 1-vinylnaphthalene, 2,vinylnaphthalene, methyl acrylate, ethyl acrylate, propyl acrylate, butyl acrylate, pentyl acrylate, hexyl acrylate, methyl methacrylate, N-(methyl)acrylamide, acrylic acid-2-ethylhexyl ester, methacrylic acid-2-ethylhexyl ester, N-(2-ethylhexyl)acrylamide, octyl acrylate, octyl methacrylate, N-(octyl)acrylamide, lauryl acrylate, lauryl methacrylate, N-(lauryl)acrylamide, stearyl acrylate, stearyl methacrylate, N-(stearyl)acrylamide, behenyl acrylate. behenyl methacrylate and N-(behenyl)acrylamide or mixtures thereof.

The proportion by weight of the sulfonic acid group-containing copolymers in the total weight of the inventive detergents or cleaning agents is preferably from 0.1 to 15 wt. %, preferably 1.0 to 12 wt. %, and in particular from 2.0 to 10 wt. %.

The detergents or cleaning agents as contemplated herein can thus be present for example in solid or liquid form, but also as a combination of solid and liquid forms, in the supplied forms known to a person skilled in the art. Suitable solid supplied forms are in particular powders, granules, extrudates or compacts, particularly tablets. The liquid supplied forms based on water and/or organic solvents may be present in thickened form, in the form of gels.

The detergents or cleaning agents as contemplated herein are preferably present in liquid form. Preferred detergents or cleaning agents contain, based on their total weight, more than 40 wt. %, preferably between 50 and 90 wt. % and in particular between 60 and 80% by weight water.

As a further component, the detergents or cleaning agents as contemplated herein may contain an organic solvent. The addition of organic solvents has an advantageous effect on the enzyme stability and the cleaning performance of these agents. Preferred organic solvents originate from the group of mono- or polyvalent alcohols, alkanolamines or glycol ethers. The solvents are preferably selected from ethanol, n- or i-propanol, butanol, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, di-ethylene glycol ethyl ether, propylene glycol methyl, ethyl or propyl ether, dipropylene glycol methyl, or ethyl ether, methoxy, ethoxy or butoxy triglycol, 1-butoxyethoxy-2 propanol, 3-methyl-3-methoxybutanol, propylene glycol t-butyl ether and mixtures of these solvents. The proportion by weight of these organic solvents in the total weight of the inventive detergents or cleaning agents is preferably 0.1 to 10 wt. %, preferably 0.2 to 8.0 wt. %, and in particular 0.5 to 5.0 wt. %. A particularly preferred organic solvent that is particularly effective with respect to the stabilization of the washing or cleaning agent is glycerol and 1,2-propylene glycol. Liquid detergents or cleaning agents which, preferably, contain at least one polyol from the group of glycerol and 1,2-propylene glycol, wherein the proportion by weight of the polyol in the total weight of the detergent or cleaning agent is preferably 0.1 to 10 wt. %, preferably 0.2 and 8.0 wt. %, and in particular 0.5 and 5.0 wt. %, are preferred as contemplated herein.

More preferred organic solvents are the organic amines and alkanolamines. The detergents or cleaning agents as contemplated herein contain these amines preferably in amounts of from 0.1 to 10 wt. %, preferably from 0.2 to 8.0 wt. %, and in particular from 0.5 to 5.0 wt. %, in each case in relation to their total weight. A particularly preferred alkanolamine is ethanolamine.

Another preferred constituent of the detergents or cleaning agents as contemplated herein is a sugar alcohol (alditol). The group of alditols includes non-cyclic polyols of the formula HOCH2[CH(OH)]nCH2OH. The alditols include, for example, mannitol, isomalt, lactitol, sorbitol and xylitol, threitol, erythritol and arabitol. With respect to the enzyme stability, sorbitol has proven to be particularly advantageous. The proportion by weight of the sugar alcohol in the total weight of the detergent or cleaning agent is preferably 1.0 to 10 wt. %, preferably 2.0 to 8.0 wt. % and in particular 3.0 to 6.0 wt. %.

Inventive liquid detergents or cleaning agents are preferably provided in multi-phase form, that is to say by combining two or more separate, different liquid detergents or cleaning agents. This type of formulation increases the stability of the detergent or cleaning agent and improves its cleaning performance. A detergent or cleaning agent that is preferred as contemplated herein is characterized in that it comprises a packaging means and two separate liquid detergents or cleaning agents A and B disposed in this packaging means, wherein the composition A contains
a) at least one inventive modified protease:
b) at least one further enzyme, different from the protease as contemplated herein:
c) from 10 to 84.9 wt. % builder(s);
d) from 15 to 89.9 wt. % water; and
the composition B contains
e) from 10 to 75 wt. % builder(s):
f) from 25 to 90 wt. % water.

Another subject as contemplated herein is a method for cleaning textiles or hard surfaces, which method is characterized in that, in at least one method step. an agent as contemplated herein is applied, or in that a protease as contemplated herein is catalytically active in at least one method step, in particular such that the protease is used in an amount of from 40 µg to 4 g, preferably from 50 µg to 3 g, particularly preferably from 100 µg to 2 g, and very particularly preferably from 200 µg to 1 g.

These include both manual and automatic methods, wherein automatic methods are preferred. Methods for cleaning textiles are generally characterized in that in several method steps various cleaning-active substances are applied to the item to be cleaned and washed off after the contact time, or in that the item to be cleaned is treated in another way with a detergent or a solution or dilution of this agent. The same is true for methods for cleaning all materials other than textiles, especially hard surfaces. All conceivable washing or cleaning methods can be enhanced in at least one of the method steps by the use of an inventive detergent or cleaning agent or a protease as contemplated herein, and then constitute embodiments of the present disclosure. All facts, subjects and embodiments described for proteases as contemplated herein and agents containing them can also be applied to this subject as contemplated herein. Therefore, reference is expressly made at this juncture to the disclosure at the appropriate place with the note that this disclosure also applies to the above method as contemplated herein.

Since proteases as contemplated herein already naturally have a hydrolytic activity and also exhibit this in media which otherwise have no cleaning power, such as in neat buffer, an individual and/or the only step of such a method can lie in that, if desired, a protease as contemplated herein can be brought into contact, as the sole cleaning-active component, with the stain, preferably in a buffer solution or in water. This represents a further embodiment of this subject as contemplated herein.

Alternative embodiments of this subject as contemplated herein also represent methods for the treatment of textile raw materials or for textile care, in which, in at least one method step, a protease as contemplated herein is active. Here, methods for textile raw materials, fibers or textiles containing natural ingredients are preferred, and very particularly for those containing wool or silk.

Another subject as contemplated herein is the use of an agent as contemplated herein for cleaning textiles or hard surfaces, or a protease as contemplated herein for cleaning textiles or hard surfaces, in particular such that the protease is used in an amount of from 40 µg to 4 g, preferably from 50 µg to 3 g, particularly preferably from 100 µg to 2 g, and very particularly preferably from 200 µg to 1 g.

All facts, subjects and embodiments described for proteases as contemplated herein and agents comprising them are also applicable to this subject as contemplated herein. Therefore, reference is expressly made at this juncture to the disclosure at the appropriate place with the note that this disclosure also applies to the above use as contemplated herein.

EXAMPLES

The following examples explain the disclosure, but without limiting it:

All molecular-biological process steps follow standard methods, such as those described in the manual by Fritsch, Sambrook and Maniatis "Molecular cloning: a laboratory manual," Cold Spring Harbor Laboratory Press, New York, 1989, or comparable relevant works enzymes. Enzymes and kits were used according to the respective manufacturers instructions.

Example 1

Starting from a protease comprising an amino acid sequence according to SEQ ID NO. 1, an inventive protease variant was prepared by site-directed mutagenesis in the nucleic acid coding for the protease nucleic acid by employing a "PHUSION Site-directed mutagenesis kit" (Finnzyme, F541). Here, the codons for the indicated amino acid positions were modified, so that an exchange of the amino acids took place as indicated, based on the amino acid sequence. The expression of the protease variant was performed in standard fashion by transforming *Bacillus licheniformis*, with an appropriate expression vector and subsequent culture of the transformants expressing the protease variant.

Protease variant 1 [SEQ ID NO. 4]: protease having an amino acid sequence according to SEQ ID NO. 1 with the amino acid substitution N97D in the numbering according to SEQ ID NO. 1;
Protease variant 2 [SEQ ID NO. 5]: protease having an amino acid sequence according to SEQ ID NO. 1 with the amino acid substitution R99E in the numbering according to SEQ ID NO. 1;
Protease variant 3 [SEQ ID NO. 6]: protease having an amino acid sequence according to SEQ ID NO. 1 with the amino acid substitutions N97D and R99E in the numbering according to SEQ ID NO. 1;

Protease variant 4 [SEQ ID NO. 7]: protease having an amino acid sequence according to SEQ ID NO. 2 with the amino acid substitution S97D in the numbering according to SEQ ID NO. 1;

Protease variant 5 [SEQ ID NO. 8]: protease having an amino acid sequence according to SEQ ID NO. 2 with the amino acid substitution S99E in the numbering according to SEQ ID NO. 1;

Protease variant 6 [SEQ ID NO. 9]: protease having an amino acid sequence according to SEQ ID NO. 2 with the amino acid substitutions S97D and S99E in the numbering according to SEQ ID NO. 1:

Example 2: Investigation of Variants 1 to 3 on a Laboratory Scale

The protease variants 1 to 3 [SEQ ID NOS. 4, 5 and 6] were produced in small laboratory fermenters using standard procedures.

The proteases were purified by ion exchange chromatography from the fermentation supernatants, and the active protein content of the resulting samples and also the specific activity were determined by titration of the active centers. The following approach was adopted accordingly with the wild-type [SEQ ID NO. 1] and the reference protease [SEQ ID NO. 3].

A first washing test was carried out on a 48-well scale on the basis of the data determined, with washing performed with the same active protein at 40° C. in a commercial-like screening formulation The following results were achieved:

|  | SEQ ID NO. 3 | SEQ ID NO. 1 | SEQ ID NO. 4 | SEQ ID NO. 5 | SEQ ID NO. 6 |
| --- | --- | --- | --- | --- | --- |
| 10N | 4.2 | 6 | 7.7 | 5.9 | 8.3 |
| C-05 | 6.2 | 6.7 | 7.8 | 6.5 | 7.4 |

It is evident that the mutation at position 97 results in an improved washing performance and in some cases the combination with the mutation at position 99 allows a further improvement.

For this example standardized soiled fabrics were used. The following stains were used:

blood and milk/ink on cotton: product no. C-05 available from CFT (Center For Test Materials) B.V. Vlaardingen. Netherlands and whole egg/pigment on cotton: product no. 10N available from wfk—Cleaning Technology Institute e.V., Krefeld, Germany.

Example 3: Investigation of Variants 1 to 3 in the Washing Machine

The protease variants 1 to 3 [SEQ ID NOS. 4, 5 and 6] and the wild-type [SEQ ID NO. 1] were washed comparatively in the washing machine.

The same amount of active enzyme was used in each case.

The proteases were dosed "on top" to an aqueous liquid detergent (containing, besides water, 5.5 wt. % 7x ethoxylated C12/14 fatty alcohol, 5.3 wt. % sodium C9-13 alkyl benzene sulfonate, 4.9 wt. % sodium C12/14 fatty alcohol ether sulfate with 2 EO, 1.8 wt. % citric acid, 3 wt. % o C12-18 fatty acid, 0.1 wt. % diethylenetriaminepenta(methylene phosphonic acid) hepta sodium salt, 1.3 wt. %6 NaOH, 3.6 wt. % ethanol/glycerol) at pH 8.5 without protease and washed at 40° C., water hardness 16° dH, in a Miele W 1935 machine, total wash time 2 h 15 min.

There was a 6-fold determination carried out and different stain monitors were washed and measured after washing using a colorimeter.

The following delta Y values were obtained compared with the wild type I SEQ ID NO. 1]:

|  | SEQ ID NO. 5 | SEQ ID NO. 4 | SEQ ID NO. 6 |
| --- | --- | --- | --- |
| 01. EMPA 111 [CO] | 3.1 | 1.6 | 9.9 |
| 03. CFT C05 [CO] | 1.9 | 2.2 | 5.1 |
| 05. WFK 10EG [CO] | 0.2 | 0.7 | 1.2 |
| 09. H-MR-B [CO] | 7.4 | 4.2 | 8.4 |
| 10. EMPA 165 [CO] | 0.8 | 0.9 | 1.4 |

Also, for this example, standardized soiled textiles were used. The following stains were used:

blood on cotton; product no. 111, available from the company Eidgenössische Material- und Prüfanstalt (EMPA) Testmaterialien A G, St. Gallen, Switzerland.

blood and milk/ink on cotton: product no. C-05 available from CFT (Center For Test Materials) B.V. Vlaardingen, Netherlands and egg yolk on cotton: product no. 10EG available from wfk—Cleaning Technology Institute e.V., Krefeld, Germany.

test fabric stained with standard dirt and made by the company of the applicant: unfinished cotton soiled with milk and soot (H-MR-B)

chocolate pudding on cotton; product no. 165, available from the company Eidgenössische Material- und Prüfanstalt (EMPA) Testmaterialien AG, St. Gallen, Switzerland.

One can clearly see that especially the mutation R99E (in variant 2, SEQ ID NO. 5) or the combination R99E and N97D (in variant 3, SEQ ID NO. 6) deliver very advantageous washing performances, as compared to their wild type [SEQ ID NO. 1].

Example 4: Examination of Variants 4 to 6 in the Washing Machine

The protease variants 4 to 6 [SEQ ID NOS. 7, 8 and 9] and the wild-type [SEQ ID NO. 1] were washed comparatively in the washing machine.

The same amount of active enzyme was used in each case.

The proteases were dosed "on top" to an aqueous liquid detergent (containing, besides water, 5.5 wt. % 7x ethoxylated C12/14 fatty alcohol, 5.3 wt. % sodium C9-13 alkyl benzene sulfonate, 4.9 wt. % sodium C12/14 fatty alcohol ether sulfate with 2 EO, 1.8 wt. % citric acid, 3 wt. % C12-18 fatty acid, 0.1 wt. %.

Diethylenetriaminepenta(methylene phosphonic acid) hepta sodium salt, 1.3 wt. % NaOH, 3.6 wt % ethanol/glycerol) were dosed at pH 8.5 without protease and washed at 40° C., water hardness 16° dH, in a Miele W 1935 machine, total wash time 2 h 15 min.

There was a 6-fold determination carried out, and different stain monitors were washed and measured after washing using a colorimeter.

There following delta Y values were obtained compared with the wild type [SEQ ID NO. 1]:

|   | SEQ ID NO. 7 | SEQ ID NO. 8 | SEQ ID NO. 9 |
|---|---|---|---|
| 01. CFT 03 | 2.6 | 1.3 | 3.2 |
| 02. CFT CS 02 | 1.1 | 0.7 | 1.5 |
| 03. CFT C10 | 2.2 | 2.5 | 3.2 |
| 04. H-MR-B | 6.3 | 5.5 | 9.5 |

Also, for this example, standardized soiled fabrics were used. The following stains were used:

Chocolate milk/soot on cotton: product no. 03 available from CFT (Center For Test Materials) B.V. Vlaardingen, Netherlands cocoa on cotton: product no. CS-02 available from CFT (Center For Testmaterials) B.V. Vlaardingen, The Netherlands, test fabric stained with standard dirt made by the company of the applicant: unfinished cotton, soiled with milk and soot (H-MR-B)

peanut oil pigment/milk on cotton: product no. C-10 available from CFT (Center For Testmaterials) B.V. Vlaardingen, Netherlands.

It is clear that all three mutants have a significantly improved performance compared to their wild type [SEQ ID NO. 1], particularly with regard to stains containing milk.

Example 5: Examination of Variants 1 to 3 (SEQ ID NOS. 4, 5, 6) in the Dishwasher A phosphate-free automatic dishwashing product in the form of a dishwasher tablet was used. The tablet weight was 19 g. The dishwashing product matrix had the following composition:

|   | Formula ranges Total | |
|---|---|---|
| Raw materials | % | g/job |
| Na citrate | 15.00-20.00 | 3.00-4.000 |
| phosphonate (HEDP) | 2.50-7.50 | 0.50-1.500 |
| MGDA | 0.00-25.00 | 0.00-5.000 |
| Na disilicate | 5.00-35.00 | 1.00-7.000 |
| Soda | 12.50-25.00 | 2.50-5.000 |
| Na percarbonate | 10.00-15.00 | 2.00-3.000 |
| bleaching catalyst (Mn-based) | 0.02-0.50 | 0.003-0.100 |
| TAED | 2.00-3.00 | 0.40-0.600 |
| Non-ionic surfactant 20-40EO end-cap mgl. | 2.50-10.00 | 0.50-2.000 |
| polycarboxylate | 5.00-10.00 | 1.00-2.000 |
| cationic copolymer | 0.25-0.75 | 0.05-0.150 |
| crosslinked PVP - disintegrant | 0.00-1.50 | 0.00-0.300 |
| protease | 1.50-5.00 | 0.30-1.000 |
| amylase | 0.50-3.00 | 0.10-0.600 |
| benzotriazole (silver protection) | 0.00-0.50 | 0.00-0.100 |
| Perfume | 0.05-0.15 | 0.01-0.030 |
| Dye solution | 0.00-1.00 | 0.00-0.200 |
| Zn acetate | 0.10-0.30 | 0.02-0.060 |
| Na sulfate | 0.00-25.00 | 0.00-5.000 |
| Water | 0.00-1.50 | 0.00-0.300 |
| pH adjusting agent (citric acid) | 1.00-1.50 | 0.20-0.300 |
| Processing aid | 0000-5.00 | 0.00-1.000 |
|   | 57.92-196.20 | 11.6-39.24 | calculated on 20-g tablet

The cleaning performance describes the ability of a dishwashing product, particularly an automatic dishwashing product, to remove an existing stain partially or completely.

The cleaning performance of the agent on three different stains was tested. Protease variants as contemplated herein according to SEQ ID NOS. 4, 5 or 6, or, as a reference, the protease having SEQ ID NO.1, were/was added to the agent as contemplated herein in each case.

The dishwashing process was performed in a Miele GSL dishwasher (program: 45° C., 8 min hold time, water hardness 21° German hardness) by IKW Standard The dishwasher tablet was placed in the dosing device before the start of the cleaning program.

The evaluation of the cleaning performance was carried out visually according to a scale of 1 to 10, wherein the value of 10 was the best score (no detectable residue). Three repetitions were performed, with 6 internal replicates per machine. The results given in Tables 1 and 2 are the average of the multiple determinations.

TABLE 1

| Protease variant | Assam tea | BOP tea | Spaghetti |
|---|---|---|---|
| SEQ ID NO. 1 | 2.3 | 3.3 | 3.8 |
| SEQ ID NO. 4 | 3.0 | 4.0 | 3.9 |
| SEQ ID NO. 5 | 2.7 | 4.4 | 3.5 |

As can be seen from Table 1, the use of the protease variants according to SEQ ID NOS. 4 and 5 leads to an improvement in the cleaning performance, in particular on tea stains.

TABLE 2

| Protease variant | Assam tea | BOP tea | Spaghetti |
|---|---|---|---|
| SEQ ID NO. 1 | 1.6 | 3.2 | 1.3 |
| SEQ ID NO. 6 | 2.0 | 3.4 | 3.1 |

As can be seen from Table 2, the use of the protease variant according to SEQ ID NO. 6 both on tea stains, and also in particular spaghetti stains, leads to an improvement in the cleaning performance.

The invention claimed is:

1. A protease comprising a polypeptide having an amino acid sequence with at least 90% identity to SEQ ID NO: 1 or 2 and having an Asp residue at position 97 and a Glu residue at position 99 wherein numbering is according to SEQ ID NO: 1.

2. The protease according to claim 1, having the sequence identical to that of SEQ ID NO: 6.

3. The protease according to claim 1, having the sequence identical to that of SEQ ID NO: 9.

4. A method for producing a protease, the method comprising the step of:

introducing amino acid substitutions N97D and R99E in the numbering according to SEQ ID NO: 1 into a starting protease identical to the amino acid sequence specified in SEQ ID NO: 1 over the total length thereof to an extent of at least 90%; or introducing amino acid substitutions S97D and S99E in the numbering according to SEQ ID NO: 1 into a starting protease identical to that specified in SEQ ID NO: 2 over the total length thereof to an extent of at 90%.

* * * * *

SEQUENCE LISTING

<160> NUMBER OF SEQ ID NOS: 9

<210> SEQ ID NO 1
<211> LENGTH: 269
<212> TYPE: PRT
<213> ORGANISM: bacillus gibsonii (dsm 14391)

<400> SEQUENCE: 1

```
Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 2
<211> LENGTH: 374
<212> TYPE: PRT
<213> ORGANISM: Bacillus sp. DSM 14392

<400> SEQUENCE: 2

Met Gly Lys Ile Val Ala Gly Thr Ala Leu Ile Ile Ser Val Ala Phe
1               5                   10                  15

Ser Ser Ser Ile Ala Gln Ala Ala Glu Ala Lys Glu Lys Tyr Leu
            20                  25                  30

Ile Gly Phe Lys Glu Gln Glu Val Met Ser Gln Phe Val Asp Gln Ile
        35                  40                  45

Asp Gly Asp Glu Tyr Ser Ile Ser Ser Gln Ala Glu Asp Val Glu Ile
    50                  55                  60

Asp Leu Leu His Glu Phe Asp Phe Ile Pro Val Leu Ser Val Glu Leu
65                  70                  75                  80

Asp Pro Glu Asp Val Asp Ala Leu Glu Leu Asp Pro Ala Ile Ala Tyr
                85                  90                  95

Ile Glu Glu Asp Ala Glu Val Thr Thr Met Gln Thr Val Pro Trp Gly
            100                 105                 110
```

```
Ile Asn Arg Val Gln Ala Pro Ile Ala Gln Ser Arg Gly Phe Thr Gly
        115                 120                 125

Thr Gly Val Arg Val Ala Val Leu Asp Thr Gly Ile Ser Asn His Ala
    130                 135                 140

Asp Leu Arg Ile Arg Gly Gly Ala Ser Phe Val Pro Gly Glu Pro Asn
145                 150                 155                 160

Ile Ser Asp Gly Asn Gly His Gly Thr His Val Ala Gly Thr Ile Ala
                165                 170                 175

Ala Leu Asn Asn Ser Ile Gly Val Leu Gly Val Ala Pro Asn Val Asp
            180                 185                 190

Leu Tyr Gly Val Lys Val Leu Gly Ala Ser Gly Ser Gly Ser Ile Ser
        195                 200                 205

Gly Ile Ala Gln Gly Leu Gln Trp Ala Ala Asn Asn Gly Met His Ile
    210                 215                 220

Ala Asn Met Ser Leu Gly Ser Ser Ala Gly Ser Ala Thr Met Glu Gln
225                 230                 235                 240

Ala Val Asn Gln Ala Thr Ala Ser Gly Val Leu Val Val Ala Ala Ser
                245                 250                 255

Gly Asn Ser Gly Ala Gly Asn Val Gly Phe Pro Ala Arg Tyr Ala Asn
            260                 265                 270

Ala Met Ala Val Gly Ala Thr Asp Gln Asn Asn Asn Arg Ala Ser Phe
        275                 280                 285

Ser Gln Tyr Gly Ala Gly Leu Asp Ile Val Ala Pro Gly Val Gly Val
    290                 295                 300

Gln Ser Thr Val Pro Gly Asn Gly Tyr Ala Ser Phe Asn Gly Thr Ser
305                 310                 315                 320

Met Ala Thr Pro His Val Ala Gly Val Ala Ala Leu Val Lys Gln Lys
                325                 330                 335

Asn Pro Ser Trp Ser Asn Val Gln Ile Arg Asn His Leu Lys Asn Thr
            340                 345                 350

Ala Thr Asn Leu Gly Asn Thr Thr Gln Phe Gly Ser Gly Leu Val Asn
        355                 360                 365

Ala Glu Ala Ala Thr Arg
    370
```

<210> SEQ ID NO 3
<211> LENGTH: 269
<212> TYPE: PRT
<213> ORGANISM: Bacillus lentus

<400> SEQUENCE: 3

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
```

```
            100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
            130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                    165                 170                 175
Asn Asn Asn Arg Ala Ser Phe Ser Gln Tyr Gly Ala Gly Leu Asp Ile
                    180                 185                 190
Val Ala Pro Gly Val Asn Val Gln Ser Thr Tyr Pro Gly Ser Thr Tyr
                    195                 200                 205
Ala Ser Leu Asn Gly Thr Ser Met Ala Thr Pro His Val Ala Gly Ala
                    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                    245                 250                 255
Tyr Gly Ser Gly Leu Val Asn Ala Glu Ala Ala Thr Arg
                    260                 265

<210> SEQ ID NO 4
<211> LENGTH: 269
<212> TYPE: PRT
<213> ORGANISM: bacillus gibsonii (dsm 14391)

<400> SEQUENCE: 4

Gln Gln Thr Val Pro Trp Gly Ile Thr Arg Val Gln Ala Pro Thr Val
1               5                   10                  15
His Asn Arg Gly Ile Thr Gly Ser Gly Val Lys Val Ala Ile Leu Asp
                    20                  25                  30
Thr Gly Ile Ala Gln His Ser Asp Leu Thr Ile Arg Gly Gly Ala Ser
                    35                  40                  45
Phe Val Pro Gly Glu Ser Thr Thr Ala Asp Leu Asn Gly His Gly Thr
50                  55                  60
His Val Ala Gly Thr Val Ala Ala Leu Asn Asn Ser Ile Gly Val Ile
65                  70                  75                  80
Gly Val Ala Pro Ser Ala Asp Leu Tyr Ala Val Lys Val Leu Gly Ala
                    85                  90                  95
Asp Gly Arg Gly Ser Val Ser Gly Ile Ala Gln Gly Leu Glu Trp Ala
                    100                 105                 110
Ala Thr Asn Asn Met His Ile Ala Asn Met Ser Leu Gly Ser Asp Ala
                    115                 120                 125
Pro Ser Thr Thr Leu Glu Arg Ala Val Asn Tyr Ala Thr Ser Arg Gly
                    130                 135                 140
Val Leu Val Ile Ala Ala Thr Gly Asn Asn Gly Thr Gly Ser Ile Gly
145                 150                 155                 160
Tyr Pro Ala Arg Tyr Ala Asn Ala Met Ala Val Gly Ala Thr Asp Gln
                    165                 170                 175
Asn Asn Arg Arg Ala Ser Phe Ser Gln Tyr Gly Thr Gly Ile Asp Ile
                    180                 185                 190
Val Ala Pro Gly Val Gly Ile Gln Ser Thr Tyr Leu Asn Asn Ser Tyr
                    195                 200                 205
```

```
Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 5
<211> LENGTH: 269
<212> TYPE: PRT
<213> ORGANISM: bacillus gibsonii (dsm 14391)

<400> SEQUENCE: 5

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Glu Gly Ser Val Ser Gly Ile Ala Gln Gly Leu Glu Trp Ala
                100                 105                 110

Ala Thr Asn Asn Met His Ile Ala Asn Met Ser Leu Gly Ser Asp Ala
            115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
    195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 6
<211> LENGTH: 269
<212> TYPE: PRT
<213> ORGANISM: bacillus gibsonii (dsm 14391)

<400> SEQUENCE: 6
```

```
Gln Gln Thr Val Pro Trp Gly Ile Thr Arg Val Gln Ala Pro Thr Val
 1               5                  10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
 50                  55                  60

His Val Ala Gly Thr Val Ala Ala Leu Asn Asn Ser Ile Gly Val Ile
 65                  70                  75                  80

Gly Val Ala Pro Ser Ala Asp Leu Tyr Ala Val Lys Val Leu Gly Ala
                85                  90                  95

Asp Gly Glu Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 7
<211> LENGTH: 374
<212> TYPE: PRT
<213> ORGANISM: Bacillus sp. DSM 14392

<400> SEQUENCE: 7

Met Gly Lys Ile Val Ala Gly Thr Ala Leu Ile Ile Ser Val Ala Phe
 1               5                  10                  15

Ser Ser Ser Ile Ala Gln Ala Ala Glu Glu Ala Lys Glu Lys Tyr Leu
            20                  25                  30

Ile Gly Phe Lys Glu Gln Glu Val Met Ser Gln Phe Val Asp Gln Ile
        35                  40                  45

Asp Gly Asp Glu Tyr Ser Ile Ser Ser Gln Ala Glu Asp Val Glu Ile
 50                  55                  60

Asp Leu Leu His Glu Phe Asp Phe Ile Pro Val Leu Ser Val Glu Leu
 65                  70                  75                  80

Asp Pro Glu Asp Val Asp Ala Leu Glu Leu Asp Pro Ala Ile Ala Tyr
                85                  90                  95

Ile Glu Glu Asp Ala Glu Val Thr Thr Met Gln Thr Val Pro Trp Gly
            100                 105                 110
```

Ile Asn Arg Val Gln Ala Pro Ile Ala Gln Ser Arg Gly Phe Thr Gly
            115                 120                 125

Thr Gly Val Arg Val Ala Val Leu Asp Thr Gly Ile Ser Asn His Ala
        130                 135                 140

Asp Leu Arg Ile Arg Gly Gly Ala Ser Phe Val Pro Gly Glu Pro Asn
145                 150                 155                 160

Ile Ser Asp Gly Asn Gly His Gly Thr His Val Ala Gly Thr Ile Ala
                165                 170                 175

Ala Leu Asn Asn Ser Ile Gly Val Leu Gly Val Ala Pro Asn Val Asp
                180                 185                 190

Leu Tyr Gly Val Lys Val Leu Gly Ala Asp Gly Ser Gly Ser Ile Ser
            195                 200                 205

Gly Ile Ala Gln Gly Leu Gln Trp Ala Ala Asn Asn Gly Met His Ile
        210                 215                 220

Ala Asn Met Ser Leu Gly Ser Ser Ala Gly Ser Ala Thr Met Glu Gln
225                 230                 235                 240

Ala Val Asn Gln Ala Thr Ala Ser Gly Val Leu Val Val Ala Ala Ser
                245                 250                 255

Gly Asn Ser Gly Ala Gly Asn Val Gly Phe Pro Ala Arg Tyr Ala Asn
            260                 265                 270

Ala Met Ala Val Gly Ala Thr Asp Gln Asn Asn Asn Arg Ala Ser Phe
        275                 280                 285

Ser Gln Tyr Gly Ala Gly Leu Asp Ile Val Ala Pro Gly Val Gly Val
290                 295                 300

Gln Ser Thr Val Pro Gly Asn Gly Tyr Ala Ser Phe Asn Gly Thr Ser
305                 310                 315                 320

Met Ala Thr Pro His Val Ala Gly Val Ala Ala Leu Val Lys Gln Lys
                325                 330                 335

Asn Pro Ser Trp Ser Asn Val Gln Ile Arg Asn His Leu Lys Asn Thr
            340                 345                 350

Ala Thr Asn Leu Gly Asn Thr Thr Gln Phe Gly Ser Gly Leu Val Asn
        355                 360                 365

Ala Glu Ala Ala Thr Arg
    370

<210> SEQ ID NO 8
<211> LENGTH: 374
<212> TYPE: PRT
<213> ORGANISM: Bacillus sp. DSM 14392

<400> SEQUENCE: 8

Met Gly Lys Ile Val Ala Gly Thr Ala Leu Ile Ile Ser Val Ala Phe
1               5                   10                  15

Ser Ser Ser Ile Ala Gln Ala Ala Glu Glu Ala Lys Glu Lys Tyr Leu
                20                  25                  30

Ile Gly Phe Lys Glu Gln Glu Val Met Ser Gln Phe Val Asp Gln Ile
            35                  40                  45

Asp Gly Asp Glu Tyr Ser Ile Ser Ser Gln Ala Glu Asp Val Glu Ile
        50                  55                  60

Asp Leu Leu His Glu Phe Asp Phe Ile Pro Val Leu Ser Val Glu Leu
65                  70                  75                  80

Asp Pro Glu Asp Val Asp Ala Leu Glu Leu Asp Pro Ala Ile Ala Tyr
                85                  90                  95

Ile Glu Glu Asp Ala Glu Val Thr Thr Met Gln Thr Val Pro Trp Gly

```
            100                 105                 110
Ile Asn Arg Val Gln Ala Pro Ile Ala Gln Ser Arg Gly Phe Thr Gly
        115                 120                 125

Thr Gly Val Arg Val Ala Val Leu Asp Thr Gly Ile Ser Asn His Ala
130                 135                 140

Asp Leu Arg Ile Arg Gly Ala Ser Phe Val Pro Gly Glu Pro Asn
145                 150                 155                 160

Ile Ser Asp Gly Asn Gly His Gly Thr His Val Ala Gly Thr Ile Ala
                165                 170                 175

Ala Leu Asn Asn Ser Ile Gly Val Leu Gly Val Ala Pro Asn Val Asp
            180                 185                 190

Leu Tyr Gly Val Lys Val Leu Gly Ala Ser Gly Glu Gly Ser Ile Ser
        195                 200                 205

Gly Ile Ala Gln Gly Leu Gln Trp Ala Ala Asn Asn Gly Met His Ile
    210                 215                 220

Ala Asn Met Ser Leu Gly Ser Ser Ala Gly Ser Ala Thr Met Glu Gln
225                 230                 235                 240

Ala Val Asn Gln Ala Thr Ala Ser Gly Val Leu Val Val Ala Ala Ser
                245                 250                 255

Gly Asn Ser Gly Ala Gly Asn Val Gly Phe Pro Ala Arg Tyr Ala Asn
            260                 265                 270

Ala Met Ala Val Gly Ala Thr Asp Gln Asn Asn Asn Arg Ala Ser Phe
        275                 280                 285

Ser Gln Tyr Gly Ala Gly Leu Asp Ile Val Ala Pro Gly Val Gly Val
    290                 295                 300

Gln Ser Thr Val Pro Gly Asn Gly Tyr Ala Ser Phe Asn Gly Thr Ser
305                 310                 315                 320

Met Ala Thr Pro His Val Ala Gly Val Ala Ala Leu Val Lys Gln Lys
                325                 330                 335

Asn Pro Ser Trp Ser Asn Val Gln Ile Arg Asn His Leu Lys Asn Thr
            340                 345                 350

Ala Thr Asn Leu Gly Asn Thr Thr Gln Phe Gly Ser Gly Leu Val Asn
        355                 360                 365

Ala Glu Ala Ala Thr Arg
    370

<210> SEQ ID NO 9
<211> LENGTH: 374
<212> TYPE: PRT
<213> ORGANISM: Bacillus sp. DSM 14392

<400> SEQUENCE: 9

Met Gly Lys Ile Val Ala Gly Thr Ala Leu Ile Ile Ser Val Ala Phe
1               5                   10                  15

Ser Ser Ser Ile Ala Gln Ala Ala Glu Glu Ala Lys Glu Lys Tyr Leu
            20                  25                  30

Ile Gly Phe Lys Glu Gln Glu Val Met Ser Gln Phe Val Asp Gln Ile
        35                  40                  45

Asp Gly Asp Glu Tyr Ser Ile Ser Ser Gln Ala Glu Asp Val Glu Ile
    50                  55                  60

Asp Leu Leu His Glu Phe Asp Phe Ile Pro Val Leu Ser Val Glu Leu
65                  70                  75                  80

Asp Pro Glu Asp Val Asp Ala Leu Glu Leu Asp Pro Ala Ile Ala Tyr
                85                  90                  95
```

```
Ile Glu Glu Asp Ala Glu Val Thr Thr Met Gln Thr Val Pro Trp Gly
            100                 105                 110

Ile Asn Arg Val Gln Ala Pro Ile Ala Gln Ser Arg Gly Phe Thr Gly
        115                 120                 125

Thr Gly Val Arg Val Ala Val Leu Asp Thr Gly Ile Ser Asn His Ala
    130                 135                 140

Asp Leu Arg Ile Arg Gly Gly Ala Ser Phe Val Pro Gly Glu Pro Asn
145                 150                 155                 160

Ile Ser Asp Gly Asn Gly His Gly Thr His Val Ala Gly Thr Ile Ala
                165                 170                 175

Ala Leu Asn Asn Ser Ile Gly Val Leu Gly Val Ala Pro Asn Val Asp
                180                 185                 190

Leu Tyr Gly Val Lys Val Leu Gly Ala Asp Gly Glu Gly Ser Ile Ser
            195                 200                 205

Gly Ile Ala Gln Gly Leu Gln Trp Ala Ala Asn Asn Gly Met His Ile
        210                 215                 220

Ala Asn Met Ser Leu Gly Ser Ser Ala Gly Ser Ala Thr Met Glu Gln
225                 230                 235                 240

Ala Val Asn Gln Ala Thr Ala Ser Gly Val Leu Val Val Ala Ala Ser
                245                 250                 255

Gly Asn Ser Gly Ala Gly Asn Val Gly Phe Pro Ala Arg Tyr Ala Asn
                260                 265                 270

Ala Met Ala Val Gly Ala Thr Asp Gln Asn Asn Asn Arg Ala Ser Phe
            275                 280                 285

Ser Gln Tyr Gly Ala Gly Leu Asp Ile Val Ala Pro Gly Val Gly Val
        290                 295                 300

Gln Ser Thr Val Pro Gly Asn Gly Tyr Ala Ser Phe Asn Gly Thr Ser
305                 310                 315                 320

Met Ala Thr Pro His Val Ala Gly Val Ala Ala Leu Val Lys Gln Lys
                325                 330                 335

Asn Pro Ser Trp Ser Asn Val Gln Ile Arg Asn His Leu Lys Asn Thr
                340                 345                 350

Ala Thr Asn Leu Gly Asn Thr Thr Gln Phe Gly Ser Gly Leu Val Asn
            355                 360                 365

Ala Glu Ala Ala Thr Arg
    370
```